(12) United States Patent
Lee et al.

(10) Patent No.: US 11,505,603 B2
(45) Date of Patent: Nov. 22, 2022

(54) ANTI-TIGIT ANTIBODIES AND USES THEREOF

(71) Applicant: YUHAN CORPORATION, Seoul (KR)

(72) Inventors: Kwang-Hoon Lee, Gyeonggi-do (KR); June Hyung Lee, Seoul (KR); Na Rae Lee, Seoul (KR); Eunjeong Jeong, Gyeonggi-do (KR); Young Bong Park, Gyeonggi-do (KR); Nakho Chang, Chungcheongbuk-do (KR); Eun-Jung Lee, Gyeonggi-do (KR); Ki Hong Kim, Gyeonggi-do (KR); Sunghyun Choi, Gyeonggi-do (KR); Byung Hyun Choi, Gyeonggi-do (KR); Ju Young Park, Seoul (KR); Moo Young Song, Gyeonggi-do (KR); Jong-Seo Lee, Gyeonggi-do (KR); Kyu-Tae Kim, Gyeonggi-do (KR); Bong-Kook Ko, Seoul (KR)

(73) Assignee: YUHAN CORPORATION, Seoul (KR)

(*) Notice: Subject to any disclaimer, the term of this patent is extended or adjusted under 35 U.S.C. 154(b) by 210 days.

(21) Appl. No.: 16/970,351

(22) PCT Filed: Feb. 28, 2019

(86) PCT No.: PCT/KR2019/002440
§ 371 (c)(1),
(2) Date: Aug. 15, 2020

(87) PCT Pub. No.: WO2019/168382
PCT Pub. Date: Sep. 6, 2019

(65) Prior Publication Data
US 2021/0087268 A1 Mar. 25, 2021

(30) Foreign Application Priority Data
Feb. 28, 2018 (KR) .................. 10-2018-0024822

(51) Int. Cl.
| | |
|---|---|
| *A61K 39/395* | (2006.01) |
| *C07K 16/00* | (2006.01) |
| *C07K 16/46* | (2006.01) |
| *C07H 21/04* | (2006.01) |
| *C12N 5/02* | (2006.01) |
| *C12N 5/20* | (2006.01) |
| *C12N 15/00* | (2006.01) |
| *C07K 16/28* | (2006.01) |
| *A61K 39/00* | (2006.01) |

(52) U.S. Cl.
CPC .... *C07K 16/2803* (2013.01); *A61K 2039/505* (2013.01); *C07K 2317/33* (2013.01); *C07K 2317/52* (2013.01); *C07K 2317/55* (2013.01); *C07K 2317/565* (2013.01); *C07K 2317/622* (2013.01); *C07K 2317/73* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 9,499,596 B2 | 11/2016 | Clark | |
| 9,713,641 B2 | 7/2017 | Hicklin et al. | |
| 2015/0216970 A1 | 8/2015 | Grogan et al. | |
| 2016/0176963 A1 | 6/2016 | Maurer et al. | |
| 2017/0037133 A1 | 2/2017 | Fiedler et al. | |
| 2017/0165366 A1 | 6/2017 | Hicklin et al. | |
| 2017/0198042 A1 | 7/2017 | Williams et al. | |

FOREIGN PATENT DOCUMENTS

| | | |
|---|---|---|
| KR | 101694832 B1 | 1/2017 |
| RU | 2015123032 A | 1/2017 |

(Continued)

OTHER PUBLICATIONS

Brown et al. Tolerance of single, but not multiple, amino acid replacements in antibody VH CDR2: a means of minimizing B cell wastage from somatic hypermutation? J. Immuno. May 1996, 3285-91. (Year: 1996).*

(Continued)

*Primary Examiner* — Maher M Haddad
(74) *Attorney, Agent, or Firm* — Hultquist, PLLC; Steven J. Hultquist

(57) ABSTRACT

Disclosed are a novel antibody specifically binding to the tumor-immunosuppressant, TIGIT (T cell immunoglobulin and immunoreceptor tyrosine-based inhibitory motif [ITIM] domain) or an antigen-binding fragment thereof, a nucleic acid encoding the antibody or the antigen-binding fragment thereof, a vector and a host cell including the nucleic acid, a method for producing the antibody or the antigen-binding fragment thereof, a pharmaceutical composition containing the antibody or the antigen-binding fragment thereof as an active ingredient, and uses of the pharmaceutical composition.

The antibody specifically binding to TIGIT or the antigen-binding fragment thereof and the pharmaceutical composition containing the same as an active ingredient are preferably used for the treatment of cancer or tumors.

17 Claims, 4 Drawing Sheets
(4 of 4 Drawing Sheet(s) Filed in Color)
Specification includes a Sequence Listing.

(56) References Cited

FOREIGN PATENT DOCUMENTS

WO     WO2016106302 A1     6/2016
WO     WO2017048824 A1     3/2017

OTHER PUBLICATIONS

Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*
Yang, H.Y., et al., "Construction of a Large Synthetic Human scFv Library with Six Diversified CDRs and High Functional Diversity", "Molecules and Cells", Feb. 28, 2009, pp. 225-235, vol. 27.
Genentech, et al., "Tiragolumag—HC/LC", Drugs and Biologies Search Results, 2016, Page(s) URL:https://integrity.clarivate.com/integrity/xmlxsl/pk_qcksrch.show_records?sessionID=1andhistory=andquery=MTIG-7192-A%20%andabbreviation=PROandlanguage=en.

* cited by examiner

SEQUENCE LISTING

<160> NUMBER OF SEQ ID NOS: 61

<210> SEQ ID NO 1
<211> LENGTH: 5
<212> TYPE: PRT
<213> ORGANISM: Artificial Sequence
<220> FEATURE:
<223> OTHER INFORMATION: Clone F04-10_Variable heavy chain CDR 1

<400> SEQUENCE: 1

Ser Tyr Tyr Met Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Clone S64-39_Variable heavy chain CDR 1

<400> SEQUENCE: 2

Asn Tyr Ala Met Ser
1               5

<210> SEQ ID NO 3
<211> LENGTH: 18
<212> TYPE: PRT
<213> ORGANISM: Artificial Sequence
<220> FEATURE:
<223> OTHER INFORMATION: Clone F04-10_Variable heavy chain CDR 2

<400> SEQUENCE: 3

Ser Ile Gly Ser Gly Ser Pro Ser Ser Thr Tyr Tyr Ala Asp Ser Val
1               5                   10                  15

Lys Gly

<210> SEQ ID NO 4
<211> LENGTH: 17
<212> TYPE: PRT
<213> ORGANISM: Artificial Sequence
<220> FEATURE:
<223> OTHER INFORMATION: Clone S64-39_Variable heavy chain CDR 2

<400> SEQUENCE: 4

Gly Ile Ser Pro Ser Gly Ser Ser Ile Tyr Tyr Ala Asp Ser Val Gln
1               5                   10                  15

Gly

<210> SEQ ID NO 5
<211> LENGTH: 18
<212> TYPE: PRT
<213> ORGANISM: Artificial Sequence
<220> FEATURE:
<223> OTHER INFORMATION: Clone F04-10_Variable heavy chain CDR 3

<400> SEQUENCE: 5

Ser Ser Tyr Ser Gly Gly Asn Gly Tyr Tyr Tyr Ala Tyr Ala Phe
1               5                   10                  15

Asp Tyr

<210> SEQ ID NO 6
<211> LENGTH: 18
<212> TYPE: PRT
<213> ORGANISM: Artificial Sequence
<220> FEATURE:

-continued

<223> OTHER INFORMATION: Clone S64-39_Variable heavy chain CDR 3

<400> SEQUENCE: 6

Ala Ile Arg Thr Cys Ser Leu Ser His Cys Tyr Tyr Tyr Gly Met
1               5                   10                  15
Asp Val

<210> SEQ ID NO 7
<211> LENGTH: 12
<212> TYPE: PRT
<213> ORGANISM: Artificial Sequence
<220> FEATURE:
<223> OTHER INFORMATION: Clone F04-10_Variable light chain CDR 1

<400> SEQUENCE: 7

Arg Ala Ser Gln Ser Val Ser Ser Ser Tyr Leu Ala
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Clone S64-39_Variable light chain CDR 1

<400> SEQUENCE: 8

Ser Ser Ser Ser Ser Asn Ile Gly Ser Asn Ala Val Asn
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Clone F04-10_Variable light chain CDR 2

<400> SEQUENCE: 9

Gly Ala Ser Ser Arg Ala Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Clone S64-39_Variable light chain CDR 2

<400> SEQUENCE: 10

Tyr Asp Asn Gln Arg Pro Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Clone F04-10_Variable light chain CDR 3

<400> SEQUENCE: 11

Gln Gln Gly Tyr His Arg Tyr Ala Thr
1               5

<210> SEQ ID NO 12
<211> LENGTH: 11
<212> TYPE: PRT
<213> ORGANISM: Artificial Sequence

```
<220> FEATURE:
<223> OTHER INFORMATION: Clone S64-39_Variable light chain CDR 3

<400> SEQUENCE: 12

Ala Thr Trp Asp Tyr Ser Leu Ser Gly Tyr Val
1               5                   10

<210> SEQ ID NO 13
<211> LENGTH: 128
<212> TYPE: PRT
<213> ORGANISM: Artificial Sequence
<220> FEATURE:
<223> OTHER INFORMATION: Clone F04-10_Variable heavy chain

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ser Ile Gly Ser Gly Ser Pro Ser Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Ser Ser Tyr Ser Gly Gly Asn Gly Tyr Tyr Tyr Tyr Ala
            100                 105                 110

Tyr Ala Phe Asp Tyr Trp Gly Gln Gly Thr Leu Val Thr Val Ser Ser
        115                 120                 125

<210> SEQ ID NO 14
<211> LENGTH: 127
<212> TYPE: PRT
<213> ORGANISM: Artificial Sequence
<220> FEATURE:
<223> OTHER INFORMATION: Clone S64-39_Variable heavy chain

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Ser Pro Ser Gly Ser Ser Ile Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Ile Arg Thr Cys Ser Leu Ser His Cys Tyr Tyr Tyr Tyr
            100                 105                 110

Gly Met Asp Val Trp Gly Gln Gly Thr Leu Val Thr Val Ser Ser
        115                 120                 125

<210> SEQ ID NO 15
<211> LENGTH: 108
```

```
<212> TYPE: PRT
<213> ORGANISM: Artificial Sequence
<220> FEATURE:
<223> OTHER INFORMATION: Clone F04-10_Variable light chain

<400> SEQUENCE: 15

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Tyr His Arg Tyr
                85                  90                  95

Ala Thr Phe Gly Gln Gly Thr Lys Val Glu Ile Lys
            100                 105

<210> SEQ ID NO 16
<211> LENGTH: 110
<212> TYPE: PRT
<213> ORGANISM: Artificial Sequence
<220> FEATURE:
<223> OTHER INFORMATION: Clone S64-39_Variable light chain

<400> SEQUENCE: 16

Gln Ser Val Leu Thr Gln Pro Pro Ser Ala Ser Gly Thr Pro Gly Gln
1               5                   10                  15

Arg Val Thr Ile Ser Cys Ser Ser Ser Ser Asn Ile Gly Ser Asn
            20                  25                  30

Ala Val Asn Trp Tyr Gln Gln Leu Pro Gly Thr Ala Pro Lys Leu Leu
        35                  40                  45

Ile Tyr Tyr Asp Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu
            100                 105                 110

<210> SEQ ID NO 17
<211> LENGTH: 125
<212> TYPE: PRT
<213> ORGANISM: Artificial Sequence
<220> FEATURE:
<223> OTHER INFORMATION: Clone F04_Variable heavy chain

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ser Ile Gly Ser Tyr Tyr Thr Tyr Tyr Ala Asp Ser Val Lys Gly
```

```
                50                  55                  60
Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Ser Ser Tyr Ser Gly Gly Asn Gly Tyr Tyr Tyr Ala Tyr Ala Phe
                100                 105                 110

Asp Tyr Trp Gly Gln Gly Thr Leu Val Thr Val Ser Ser
        115                 120                 125

<210> SEQ ID NO 18
<211> LENGTH: 108
<212> TYPE: PRT
<213> ORGANISM: Artificial Sequence
<220> FEATURE:
<223> OTHER INFORMATION: Clone F04_Variable light chain

<400> SEQUENCE: 18

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Tyr His Arg Tyr
                 85                  90                  95

Ala Thr Phe Gly Gln Gly Thr Lys Val Glu Ile Lys
                100                 105

<210> SEQ ID NO 19
<211> LENGTH: 127
<212> TYPE: PRT
<213> ORGANISM: Artificial Sequence
<220> FEATURE:
<223> OTHER INFORMATION: Clone S64_Variable heavy chain

<400> SEQUENCE: 19

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                20                  25                  30

Ala Met Ser Trp Val Arg Gln Ala Pro Gly Lys Gly Leu Glu Trp Val
            35                  40                  45

Ser Ala Ile Tyr Pro Gly Gly Gly Ser Ile Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ala Ile Arg Thr Cys Ser Leu Ser His Cys Tyr Tyr Tyr Tyr
                100                 105                 110

Gly Met Asp Val Trp Gly Gln Gly Thr Leu Val Thr Val Ser Ser
        115                 120                 125
```

```
<210> SEQ ID NO 20
<211> LENGTH: 111
<212> TYPE: PRT
<213> ORGANISM: Artificial Sequence
<220> FEATURE:
<223> OTHER INFORMATION: Clone S64_Variable light chain

<400> SEQUENCE: 20

Gln Ser Val Leu Thr Gln Pro Pro Ser Ala Ser Gly Thr Pro Gly Gln
1               5                   10                  15

Arg Val Thr Ile Ser Cys Ser Cys Ser Ser Asn Ile Gly Asn Asn
            20                  25                  30

Ala Val Ser Trp Tyr Gln Gln Leu Pro Gly Thr Ala Pro Lys Leu Leu
        35                  40                  45

Ile Tyr Tyr Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Ala Tyr Val Phe Gly Gly Gly Thr Lys Leu Thr Val Leu Gly
            100                 105                 110

<210> SEQ ID NO 21
<211> LENGTH: 244
<212> TYPE: PRT
<213> ORGANISM: Artificial Sequence
<220> FEATURE:
<223> OTHER INFORMATION: T-cell immunoreceptor with Ig and ITIM domains
      precursor [Homo sapiens]

<400> SEQUENCE: 21

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
```

```
            195                 200                 205
Gly Leu Cys Gly Glu Gln Arg Gly Glu Asp Cys Ala Glu Leu His Asp
    210                 215                 220
Tyr Phe Asn Val Leu Ser Tyr Arg Ser Leu Gly Asn Cys Ser Phe Phe
225                 230                 235                 240
Thr Glu Thr Gly

<210> SEQ ID NO 22
<211> LENGTH: 5
<212> TYPE: PRT
<213> ORGANISM: Artificial Sequence
<220> FEATURE:
<223> OTHER INFORMATION: Synthetic construct

<400> SEQUENCE: 22

Gly Tyr Tyr Met Ser
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic construct

<400> SEQUENCE: 23

Tyr Tyr Tyr Met Ser
1               5

<210> SEQ ID NO 24
<211> LENGTH: 15
<212> TYPE: PRT
<213> ORGANISM: Artificial Sequence
<220> FEATURE:
<223> OTHER INFORMATION: Synthetic construct

<400> SEQUENCE: 24

Ser Ile Gly Ser Tyr Tyr Thr Tyr Tyr Ala Asp Ser Val Lys Gly
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic construct

<400> SEQUENCE: 25

Ser Ile Gly Ser Tyr Tyr Ser Thr Tyr Tyr Ala Asp Ser Val Lys Gly
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic construct

<400> SEQUENCE: 26

Ser Ile Gly Ser Ser Tyr Ser Thr Tyr Tyr Ala Asp Ser Val Lys Gly
1               5                   10                  15

<210> SEQ ID NO 27
<211> LENGTH: 16
<212> TYPE: PRT
```

```
<213> ORGANISM: Artificial Sequence
<220> FEATURE:
<223> OTHER INFORMATION: Synthetic construct

<400> SEQUENCE: 27

Ser Ile Gly Gly Tyr Ser Tyr Thr Tyr Tyr Ala Asp Ser Val Lys Gly
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Synthetic construct

<400> SEQUENCE: 28

Ser Ile Gly Ser Tyr Ser Ser Thr Tyr Tyr Ala Asp Ser Val Lys Gly
1               5                   10                  15

<210> SEQ ID NO 29
<211> LENGTH: 17
<212> TYPE: PRT
<213> ORGANISM: Artificial Sequence
<220> FEATURE:
<223> OTHER INFORMATION: Synthetic construct

<400> SEQUENCE: 29

Ser Ile Gly Tyr Gly Ser Gly Tyr Thr Tyr Tyr Ala Asp Ser Val Lys
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: Synthetic construct

<400> SEQUENCE: 30

Ser Ile Gly Gly Gly Ser Ser Tyr Thr Tyr Tyr Ala Asp Ser Val Lys
1               5                   10                  15

Gly

<210> SEQ ID NO 31
<211> LENGTH: 5
<212> TYPE: PRT
<213> ORGANISM: Artificial Sequence
<220> FEATURE:
<223> OTHER INFORMATION: Synthetic construct

<400> SEQUENCE: 31

Asp Tyr Ala Met Asn
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic construct

<400> SEQUENCE: 32

Asp Tyr Ala Met Ser
1               5
```

```
<210> SEQ ID NO 33
<211> LENGTH: 5
<212> TYPE: PRT
<213> ORGANISM: Artificial Sequence
<220> FEATURE:
<223> OTHER INFORMATION: Synthetic construct

<400> SEQUENCE: 33

Asn Tyr Ser Met Ser
1               5

<210> SEQ ID NO 34
<211> LENGTH: 17
<212> TYPE: PRT
<213> ORGANISM: Artificial Sequence
<220> FEATURE:
<223> OTHER INFORMATION: Synthetic construct

<400> SEQUENCE: 34

Ser Ile Ser Pro Ser Ser Gly Ser Thr Tyr Tyr Ala Asp Ser Val Lys
1               5                   10                  15

Gly

<210> SEQ ID NO 35
<211> LENGTH: 17
<212> TYPE: PRT
<213> ORGANISM: Artificial Sequence
<220> FEATURE:
<223> OTHER INFORMATION: Synthetic construct

<400> SEQUENCE: 35

Ala Ile Ser Pro Gly Ser Gly Asn Thr Tyr Tyr Ala Asp Ser Val Lys
1               5                   10                  15

Gly

<210> SEQ ID NO 36
<211> LENGTH: 17
<212> TYPE: PRT
<213> ORGANISM: Artificial Sequence
<220> FEATURE:
<223> OTHER INFORMATION: Synthetic construct

<400> SEQUENCE: 36

Gly Ile Tyr Pro Ser Gly Gly Asn Thr Tyr Tyr Ala Asp Ser Val Lys
1               5                   10                  15

Gly

<210> SEQ ID NO 37
<211> LENGTH: 17
<212> TYPE: PRT
<213> ORGANISM: Artificial Sequence
<220> FEATURE:
<223> OTHER INFORMATION: Synthetic construct

<400> SEQUENCE: 37

Ser Ile Tyr Pro Asn Gly Gly Ser Lys Tyr Tyr Ala Asp Ser Val Lys
1               5                   10                  15

Gly

<210> SEQ ID NO 38
<211> LENGTH: 17
<212> TYPE: PRT
<213> ORGANISM: Artificial Sequence
<220> FEATURE:
<223> OTHER INFORMATION: Synthetic construct
```

-continued

<400> SEQUENCE: 38

Leu Ile Tyr Pro Ser Gly Gly Ser Lys Tyr Tyr Ala Asp Ser Val Lys
1               5                   10                  15

Gly

<210> SEQ ID NO 39
<211> LENGTH: 17
<212> TYPE: PRT
<213> ORGANISM: Artificial Sequence
<220> FEATURE:
<223> OTHER INFORMATION: Synthetic construct

<400> SEQUENCE: 39

Ser Ile Tyr Pro Ser Gly Gly Ser Lys Tyr Tyr Ala Asp Ser Val Lys
1               5                   10                  15

Gly

<210> SEQ ID NO 40
<211> LENGTH: 17
<212> TYPE: PRT
<213> ORGANISM: Artificial Sequence
<220> FEATURE:
<223> OTHER INFORMATION: Synthetic construct

<400> SEQUENCE: 40

Gly Ile Tyr Pro Ser Gly Gly Ser Thr Tyr Tyr Ala Asp Ser Val Lys
1               5                   10                  15

Gly

<210> SEQ ID NO 41
<211> LENGTH: 17
<212> TYPE: PRT
<213> ORGANISM: Artificial Sequence
<220> FEATURE:
<223> OTHER INFORMATION: Synthetic construct

<400> SEQUENCE: 41

Trp Ile Ser Pro Ser Ser Gly Ser Ile Tyr Tyr Ala Asp Ser Val Gln
1               5                   10                  15

Gly

<210> SEQ ID NO 42
<211> LENGTH: 13
<212> TYPE: PRT
<213> ORGANISM: Artificial Sequence
<220> FEATURE:
<223> OTHER INFORMATION: Synthetic construct

<400> SEQUENCE: 42

Ser Cys Ser Ser Ser Asn Ile Gly Asn Asn Ala Val Ser
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Synthetic construct

<400> SEQUENCE: 43

Ser Gly Phe Ser Ser Asn Ile Gly Asn Asn Ala Val Asn
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetic construct

<400> SEQUENCE: 44

Thr Gly Ser Ser Ser Asn Ile Gly Ser Asn Tyr Val Ser
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Synthetic construct

<400> SEQUENCE: 45

Ser Gly Ser Ser Ser Asn Ile Gly Asn Asn Tyr Val Ser
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthetic construct

<400> SEQUENCE: 46

Ser Gly Ser Ser Ser Asn Ile Gly Ser Asn Thr Phe Asn
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Synthetic construct

<400> SEQUENCE: 47

Ser Ser Ser Ser Ser Asn Ile Gly Ser Asn Tyr Val Ser
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic construct

<400> SEQUENCE: 48

Ser Gly Ser Ser Ser Asn Ile Gly Ser Asn Tyr Val Ser
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Synthetic construct

<400> SEQUENCE: 49

Tyr Asp Ser Asn Arg Pro Ser
1               5

```
<210> SEQ ID NO 50
<211> LENGTH: 7
<212> TYPE: PRT
<213> ORGANISM: Artificial Sequence
<220> FEATURE:
<223> OTHER INFORMATION: Synthetic construct

<400> SEQUENCE: 50

Tyr Asp Asn Lys Arg Pro Ser
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic construct

<400> SEQUENCE: 51

Ala Asp Ser Gln Arg Pro Ser
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic construct

<400> SEQUENCE: 52

Ala Asp Asn Asn Arg Pro Ser
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic construct

<400> SEQUENCE: 53

Ala Asp Ser His Arg Pro Ser
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic construct

<400> SEQUENCE: 54

Ala Asp Ser Asn Arg Pro Ser
1               5

<210> SEQ ID NO 55
<211> LENGTH: 11
<212> TYPE: PRT
<213> ORGANISM: Artificial Sequence
<220> FEATURE:
<223> OTHER INFORMATION: Synthetic construct

<400> SEQUENCE: 55

Gly Ser Trp Asp Tyr Ser Leu Ser Ala Tyr Val
1               5                   10

<210> SEQ ID NO 56
```

```
<211> LENGTH: 11
<212> TYPE: PRT
<213> ORGANISM: Artificial Sequence
<220> FEATURE:
<223> OTHER INFORMATION: Synthetic construct

<400> SEQUENCE: 56

Gly Thr Trp Asp Tyr Ser Leu Ser Ala Tyr Val
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic construct

<400> SEQUENCE: 57

Gly Thr Trp Asp Tyr Ser Leu Asn Gly Tyr Val
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic construct

<400> SEQUENCE: 58

Gly Thr Trp Asp Ser Ser Leu Ser Ala Tyr Val
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Synthetic construct

<400> SEQUENCE: 59

Gly Ala Trp Asp Ala Ser Leu Ser Ala Tyr Val
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthetic construct

<400> SEQUENCE: 60

Gly Ala Trp Asp Tyr Ser Leu Asn Ala Tyr Val
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Synthetic construct

<400> SEQUENCE: 61

Gly Ala Trp Asp Ser Ile Leu Ile Ala Tyr Val
1               5                   10
```

ANTI-TIGIT ANTIBODIES AND USES THEREOF

CROSS-REFERENCE TO RELATED APPLICATIONS

This application is a U.S. national phase under the provisions of 35 U.S.C. § 371 of International Patent Application No. PCT/KR19/02440 filed Feb. 28, 2019, which in turn claims priority of Korean Patent Application No. 10-2018-0024822 filed Feb. 28, 2018. The disclosures of International Patent Application No. PCT/KR19/02440 and Korean Patent Application No. 10-2018-0024822 are hereby incorporated herein by reference in their respective entireties, for all purposes.

REFERENCE TO SEQUENCE LISTING SUBMITTED VIA EFS-WEB

This application includes an electronically submitted sequence listing in .txt format. The .txt file contains a sequence listing entitled "527_SequenceListing_ST25.txt" created on Jul. 24, 2022 and is 23,290 bytes in size. The sequence listing contained in this .txt file is part of the specification and is hereby incorporated by reference herein in its entirety.

TECHNICAL FIELD

The present invention relates to a novel antibody specifically binding to the tumor-immunosuppressant, TIGIT (T cell immunoglobulin and immunoreceptor tyrosine-based inhibitory motif [ITIM] domain) or an antigen-binding fragment thereof, a nucleic acid encoding the antibody or the antigen-binding fragment thereof, a vector and a host cell including the nucleic acid, a method for producing the antibody or the antigen-binding fragment thereof, a pharmaceutical composition containing the antibody or the antigen-binding fragment thereof as an active ingredient, and uses of the pharmaceutical composition.

The antibody or the antigen-binding fragment thereof specifically binding to TIGIT, and the pharmaceutical composition containing the same as an active ingredient are preferably used for the treatment of cancer or tumors, but the present invention is not limited thereto.

BACKGROUND ART

The human immune system functions to protect human bodies by attacking pathogens or viruses (antigens) that enter from the outside and abnormal cells such as cancer cells. That is, the main function of the human immune system is to distinguish between normal cells in the body and external invaders, abnormal cells such as cancer cells, and determine whether to attack the cells. Representative immune cells that can distinguish cancer cells in the human immune system are T-cells and healthy humans can effectively kill cancer cells through immune responses although the cancer cells grow in the body. Accordingly, the progression of cancer means that the immune system is abnormal.

The human immune system has an immune detection system to inhibit hyperimmune responses caused by hyperproliferation of T-cells. Such an immune detection system is referred to as "immune checkpoint" and the proteins involved in the immune checkpoint are referred to as "immune checkpoint proteins".

Essentially, the immune checkpoint functions to inhibit hyperimmune responses by hyperactivation and/or hyperproliferation of T-cells, but cancer cells abuse the immune checkpoint to prevent T-cells from attacking the cancer cells, ultimately resulting in progression of cancer.

It is already known in the art that diseases such as cancer can be treated using inhibitors of such immune checkpoint. Currently, antibody drugs targeting immune checkpoint proteins are commercially available and various immune checkpoint inhibitors are under development.

The first developed immune checkpoint inhibitor-type therapeutic agent is ipilimumab, which is a monoclonal antibody specific to CTLA-4 (cytotoxic T-lymphocyte associated antigen-4), the immune checkpoint receptor, and was shown to be effective in metastatic malignant melanoma. Subsequently, monoclonal antibodies specific to PD-1 (programmed cell death-1) and PD-L1 (programmed death ligand-1), which are ligands for PD-1, have been developed. Representative examples thereof include nivolumab, pembrolizumab, avelumab, atezolizumab and durvalumab. PD-1 or PD-L1 inhibitors are effective in malignant melanomas as well as in a variety of tumors.

TIGIT (T-cell immunoglobulin and immunoreceptor tyrosine-based inhibitory motif [ITIM] domain) is a receptor expressed mainly in activated T cells and NK (natural killer) cells, and is included in immune checkpoint proteins in a broad sense.

TIGIT binds to ligands such as CD155 and CD112 on the surface of cancer cells to inhibit the activation of immune cells. Antibodies targeting TIGIT have been reported to induce activation of $CD8^+$ T cells together with PD-1/PD-L1 blocking antibodies and thereby to effectively remove tumors or viruses.

Several anti-TIGIT antibodies have been reported to date (such as U.S. Pat. No. 9,713,641B, US 2016/0176963A, U.S. Pat. No. 9,499,596B), but research on specific mechanisms thereof is insufficient and an antibody having an efficacy practically applicable to therapeutic agents has not yet been developed. Thus, there is still an increasing need for TIGIT-specific antibodies having high efficacies.

Accordingly, as a result of intensive efforts to develop a novel antibody specifically binding to TIGIT, the present inventors have invented a novel anti-TIGIT antibody having high affinity for TIGIT overexpressed in cancer cells and identified the potential possibility of the antibody or an antigen-binding fragment thereof according to the present invention as an efficient anticancer drug, thus completing the present invention.

PRIOR ART DOCUMENT

U.S. Pat. No. 9,713,641 (2017 Jul. 25.)
US Publication No. 2016/0176963 (2016 Jun. 23.)
U.S. Pat. No. 9,499,596 (2016 Nov. 22.)

DISCLOSURE

Technical Problem

Therefore, it is one object of the present invention to provide a novel anti-TIGIT antibody or an antigen-binding fragment thereof specifically binding to TIGIT.

It is another object of the present invention to provide a pharmaceutical composition, in particular, a pharmaceutical composition for an immune anticancer drug (immuno-oncology drug) containing the anti-TIGIT antibody or the antigen-binding fragment thereof as an active ingredient.

It is another object of the present invention to provide a method for treating a cancer or tumor including administering the anti-TIGIT antibody or the antigen-binding fragment thereof, the use of the anti-TIGIT antibody or the antigen-binding fragment thereof for the treatment of a cancer or tumor, and the use of the anti-TIGIT antibody or the antigen-binding fragment thereof for the preparation of a drug for treating a cancer or tumor.

It is another object of the present invention to provide a composition for co-administration for treating a cancer or tumor containing the anti-TIGIT antibody or the antigen-binding fragment thereof, and other therapeutic agent for cancer.

It is another object of the present invention to provide a nucleic acid encoding the anti-TIGIT antibody or the antigen-binding fragment thereof, a vector and a host cell containing the nucleic acid, and a method for producing an anti-TIGIT antibody or an antigen-binding fragment thereof using the same.

Technical Solution

In accordance with the present invention, the above and other objects can be accomplished by the provision of an anti-TIGIT antibody or an antigen-binding fragment thereof including a heavy chain variable region including a heavy chain CDR1 including an amino acid sequence set forth in SEQ ID NO: 1 or 2, a heavy chain CDR2 including an amino acid sequence set forth in SEQ ID NO: 3 or 4, and a heavy chain CDR3 including an amino acid sequence set forth in SEQ ID NO: 5 or 6, and a light chain variable region including a light chain CDR1 including an amino acid sequence set forth in SEQ ID NO: 7 or 8, a light chain CDR2 including an amino acid sequence set forth in SEQ ID NO: 9 or 10, and a light chain CDR3 including an amino acid sequence set forth in SEQ ID NO: 11 or 12.

The anti-TIGIT antibody or the antigen-binding fragment thereof may include a heavy chain variable region including an amino acid sequence set forth in SEQ ID NO: 13 or 14, and a light chain variable region including an amino acid sequence set forth in SEQ ID NO: 15 or 16.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and other advantages of the present invention will be more clearly understood from the following detailed description taken in conjunction with the accompanying drawings, in which.

DETAILED DESCRIPTION OF THE INVENTION

Figure 1:
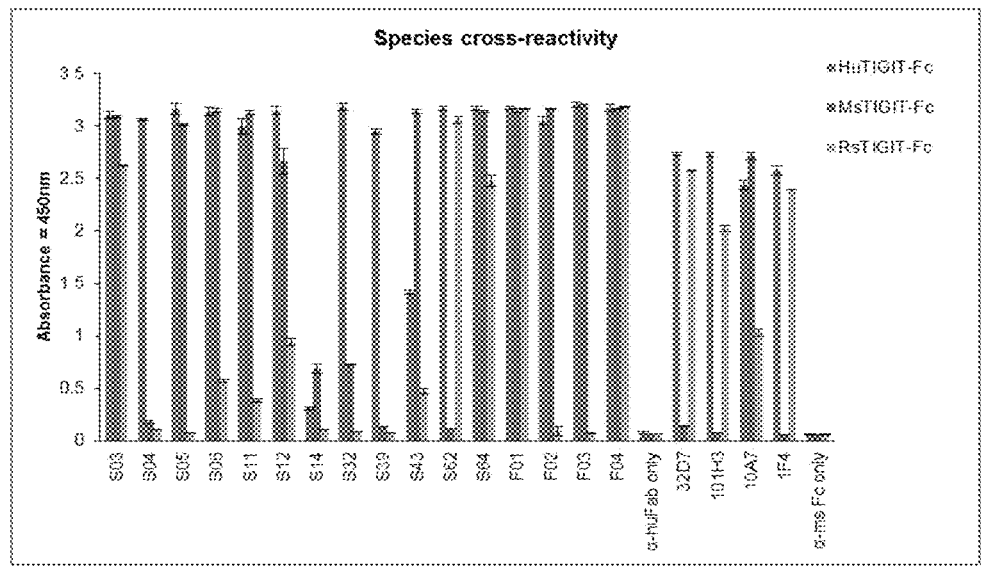
FIG. 1 shows the results of ELISA to identify binding of anti-TIGIT antibodies to human, mouse and rhesus TIGIT antigens in order to determine the species cross-reactivity of initially screened anti-TIGIT antibodies.

Unless defined otherwise, all technical and scientific terms used herein have the same meaning as appreciated by those skilled in the field to which the present invention pertains. In general, nomenclature used herein is well-known in the art and is ordinarily used.

In one aspect, the present invention relates to an anti-TIGIT antibody or an antigen-binding fragment thereof including:

a heavy chain variable region including:
a heavy chain CDR1 including an amino acid sequence set forth in SEQ ID NO: 1 or 2;
a heavy chain CDR2 including an amino acid sequence set forth in SEQ ID NO: 3 or 4; and
a heavy chain CDR3 including an amino acid sequence set forth in SEQ ID NO: 5 or 6; and
a light chain variable region including:
a light chain CDR1 including an amino acid sequence set forth in SEQ ID NO: 7 or 8;
a light chain CDR2 including an amino acid sequence set forth in SEQ ID NO: 9 or 10; and
a light chain CDR3 including an amino acid sequence set forth in SEQ ID NO: 11 or 12.

In addition, the anti-TIGIT antibody or the antigen-binding fragment thereof according to the present invention includes: a heavy chain variable region including an amino acid sequence set forth in SEQ ID NO: 13 or 14; and a light chain variable region including an amino acid sequence set forth in SEQ ID NO: 15 or 16.

Preferably, the anti-TIGIT antibody or the antigen-binding fragment thereof according to the present invention includes:

(1) a heavy chain variable region including a heavy chain CDR1 including the amino acid sequence set forth in SEQ ID NO: 1; a heavy chain CDR2 including the amino acid sequence set forth in SEQ ID NO: 3; and a heavy chain CDR3 including the amino acid sequence set forth in SEQ ID NO: 5; and a light chain variable region including a light chain CDR1 including the amino acid sequence set forth in SEQ ID NO: 7; a light chain CDR2 including the amino acid sequence set forth in SEQ ID NO: 9; and a light chain CDR3 including the amino acid sequence set forth in SEQ ID NO: 11; or (2) a heavy chain variable region including a heavy chain CDR1 including the amino acid sequence set forth in SEQ ID NO: 2; a heavy chain CDR2 including the amino acid sequence set forth in SEQ ID NO: 4; and a heavy chain CDR3 including the amino acid sequence set forth in SEQ ID NO: 6; and a light chain variable region including a light chain CDR1 including the amino acid sequence set forth in SEQ ID NO: 8; a light chain CDR2 including the amino acid sequence set forth in SEQ ID NO: 10; and a light chain CDR3 including the amino acid sequence set forth in SEQ ID NO: 12; or (3) a heavy chain variable region including the amino acid sequence set forth in SEQ ID NO: 13; and a light chain variable region including the amino acid sequence set forth in SEQ ID NO: 15; or (4) a heavy chain variable region including the amino acid sequence set forth in SEQ ID NO: 14; and a light chain variable region including the amino acid sequence set forth in SEQ ID NO: 16.

TIGIT, which is expressed on the surface of immune cells such as T cells, NK cells and dendritic cells, binds to the PVR (poliovirus receptor, CD155) on the surface of cancer cells to inhibit the activity of the immune cells. The anti-TIGIT antibody or the antigen-binding fragment thereof according to the present invention specifically binds to the CD155 binding site of TIGIT and inhibits signal transmission by TIGIT/CD155 interaction to induce activation of immune cells and inhibit growth of tumor cells. CD155 is expressed on the cell surface of various mammals such as humans, monkeys, mice and rats, and transmits signals that inhibit the activation of immune cells by binding to TIGIT.

That is, the anti-TIGIT antibody or the antigen-binding fragment thereof according to the present invention inhibits signal transmission by TIGIT/CD155 interaction to offset inhibition signals of immune cells by the cancer cells, to induce reactivation of the immune response to effectively attack the cancer cells and thereby provide anticancer effects. Ultimately, the anti-TIGIT antibody or the antigen-binding fragment thereof can be used for immune anti-cancer therapy targeting TIGIT, a tumor immunosuppressant. In particular, the anti-TIGIT antibody or the antigen-binding fragment thereof according to the present invention reduces or inhibits the expression or activity of TIGIT in a subject having cancer and induces a continuous anti-cancer response of T cells or NK cells, thereby providing an effect of treating cancer.

The TIGIT protein acting as an antigen of the anti-TIGIT antibody or the antigen-binding fragment thereof according to the present invention is closely related to the inhibition of the activity of the immune cells, is a membrane protein present on the surface of immune cells, and serves as a sub-inhibitory receptor for immune cells. The TIGIT may be derived from mammals such as primates including humans and monkeys, and rodents including mice and rats.

As used herein, the term "TIGIT" is a generic term for any variant, isoform or species homologue of TIGIT that is naturally expressed by a cell, is preferably a human TIGIT, but the present invention is not limited thereto and includes TIGIT of other animals and the like.

The anti-TIGIT antibody according to the present invention preferably binds specifically to a CD155 binding site or a CD155 binding-inhibitory site of human TIGIT (hTIGIT; SEQ ID NO: 21; NCBI accession No. NP 776160), but the present invention is not limited thereto.

The amino acid sequences and the variable region sequences of the heavy chain CDRs and light chain CDRs of the anti-TIGIT antibody or the antigen-binding fragment thereof according to the present invention are as shown in Tables 1 to 4.

TABLE 1

Amino acid sequences of heavy chain CDRs of anti-TIGIT antibody according to the invention

| CDRH1 | CDRH2 | CDRH3 |
|---|---|---|
| SYYMS (SEQ ID NO: 1) | SIGSGSPSSTYYADSVKG (SEQ ID NO: 3) | SSYSGGNGYYYYAYAFDY (SEQ ID NO: 5) |
| NYAMS (SEQ ID No: 2) | GISPSGSSIYYADSVQG (SEQ ID NO: 4) | AIRTCSLSHCYYYYGMDV (SEQ ID NO: 6) |

TABLE 2

Amino acid sequences of light chain CDRs of anti-TIGIT antibody according to the invention

| CDRL1 | CDRL2 | CDRL3 |
|---|---|---|
| RASQSVSSSYLA (SEQ ID NO: 7) | GASSRAT (SEQ ID NO: 9) | QQGYHRYAT (SEQ ID NO: 11) |
| SSSSSNIGSNAVN (SEQ ID NO: 8) | YDNQRPS (SEQ ID NO: 10) | ATWDYSLSGYV (SEQ ID NO: 12) |

TABLE 3

Amino acid sequences of heavy chain variable regions of anti-TIGIT antibody according to the present invention (CDR region is underlined)

EVQLLESGGGLVQPGGSLRLSCAASGFTFS<u>SYYMS</u>WVRQAPGKGLEWVS<u>S IGSGSPSSTYYADSVKG</u>RFTISRDNSKNTLYLQMNSLRAEDTAVYYCAR<u>S SYSGGNGYYYYAYAFDY</u>WGQGTLVTVSS (SEQ ID NO: 13)

TABLE 3-continued

Amino acid sequences of heavy chain variable
regions of anti-TIGIT antibody according to the
present invention (CDR region is underlined)

EVQLLESGGGLVQPGGSLRLSCAASGFTFS<u>NYAMS</u>WVRQAPGKGLEWVSG
<u>ISPSGSSIYYADSV</u>QGRFTISRDNSKNTLYLQMNSLRAEDTAVYYCAK<u>AI
RTCSLSHCYYYYGMDV</u>WGQGTLVTVSS (SEQ ID NO: 14)

TABLE 4

Amino acid sequences of light chain variable
regions of anti-TIGIT antibody according to the
present invention (CDR region is underlined)

EIVLTQSPGTLSLSPGERATLSC<u>RASQSVSSSYLA</u>WYQQKPGQAPRLLIY
<u>GASSRAT</u>GIPDRFSGSGSGTDFTLTISRLEPEDFAVYYC<u>QQGYHRYAT</u>FG
QGTKVEIK(SEQ ID NO: 15)

QSVLTQPPSASGTPGQRVTISC<u>SSSSSNIGSNAVN</u>WYQQLPGTAPKLLIY
<u>YDNQRPS</u>GVPDRFSGSKSGTSASLAISGLRSEDEADYYC<u>ATWDYSLSGYV</u>
FGGGTKLTVL (SEQ ID NO: 16)

Meanwhile, the anti-TIGIT antibody or the antigen-binding fragment thereof according to the present invention includes a heavy chain variable region having a sequence identity of 80% or more, preferably 90% or more, more preferably 99% or more, with each of a heavy chain CDR1 including an amino acid sequence set forth in SEQ ID NO: 1 or 2; a heavy chain CDR2 including an amino acid sequence set forth in SEQ ID NO: 3 or 4; and a heavy chain CDR3 including an amino acid sequence set forth in SEQ ID NO: 5 or 6, and an antibody or an antigen-binding fragment thereof having the same characteristics as TIGIT according to the present invention also falls within the scope of the anti-TIGIT antibody or an antigen-binding fragment thereof according to the present invention.

The anti-TIGIT antibody or an antigen-binding fragment thereof according to the present invention includes a heavy chain variable region having a sequence identity of 80% or more, preferably 90% or more, more preferably 99% or more, with a heavy chain variable region including an amino acid sequence set forth in SEQ ID NO: 13 or 14, and an antibody or an antigen-binding fragment thereof having the same characteristics as TIGIT according to the present invention also falls within the scope of the anti-TIGIT antibody or an antigen-binding fragment thereof according to the present invention.

In addition, the anti-TIGIT antibody or the antigen-binding fragment thereof according to the present invention includes a light chain variable region having a sequence identity of 80% or more, preferably 90% or more, more preferably 99% or more, with each of a light chain variable region including a light chain CDR1 including an amino acid sequence set forth in SEQ ID NO: 7 or 8, a light chain CDR2 including an amino acid sequence set forth in SEQ ID NO: 9 or 10, and a light chain CDR3 including an amino acid sequence set forth in SEQ ID NO: 11 or 12, and an antibody or an antigen-binding fragment thereof having the same characteristics as TIGIT according to the present invention also falls within the scope of the anti-TIGIT antibody or an antigen-binding fragment thereof according to the present invention.

In addition, the anti-TIGIT antibody or the antigen-binding fragment thereof includes a light chain variable region having a sequence identity of 80% or more, preferably 90% or more, more preferably 99% or more, with each of a light chain variable region including an amino acid sequence set forth in SEQ ID NO: 15 or 16, and an antibody or an antigen-binding fragment thereof having the same characteristics as TIGIT according to the present invention also falls within the scope of the anti-TIGIT antibody or an antigen-binding fragment thereof according to the present invention.

In addition, the anti-TIGIT antibody or the antigen-binding fragment thereof according to the present invention may also include an antibody or an antigen-binding fragment thereof wherein a part of the amino acid sequence of the anti-TIGIT antibody or the antigen-binding fragment thereof according to the present invention is substituted through conservative substitution.

As used herein, the term "conservative substitution" refers to modification of a polypeptide including substituting one or more amino acids by one or more amino acids having similar biological or biochemical properties that do not cause loss of the biological or biochemical functions of the polypeptide. The term "conservative amino acid substitution" refers to a substitution to replace an amino acid residue by an amino acid residue having a similar side chain. Classes of the amino acid residue having a similar side chain are defined and well-known in the art. Such classes include amino acids with basic side chains (e.g., lysine, arginine, histidine), amino acids with acidic side chains (e.g., aspartic acid, glutamic acid), amino acids with uncharged polar side chains (e.g., glycine, asparagine, glutamine, serine, threonine, tyrosine, cysteine), amino acids having non-polar side chains (e.g., alanine, valine, leucine, isoleucine, proline, phenylalanine, methionine, tryptophan), amino acids having beta-branched side chains (e.g., threonine, valine, isoleucine) and amino acids having aromatic side chains (e.g., tyrosine, phenylalanine, tryptophan, histidine). It is considered that the antibody according to the present invention has a conservative amino acid substitution and still retains activity.

As used herein, the term "TIGIT-specific antibody" refers to an antibody that binds to TIGIT to inhibit the biological activity of TIGIT, which is used interchangeably with "anti-TIGIT antibody".

As used herein, the term "anti-TIGIT antibody" includes both a polyclonal antibody and a monoclonal antibody, is preferably a monoclonal antibody and may have a whole antibody. The whole antibody is a structure having two full-length light chains and two full-length heavy chains, and including a constant region, wherein each light chain is linked to the corresponding heavy chain by a disulfide bond.

The whole antibody of the anti-TIGIT antibody according to the present invention includes IgA, IgD, IgE, IgM and IgG forms, and IgG includes subtypes IgG1, IgG2, IgG3 and IgG4.

The anti-TIGIT antibody according to the present invention is preferably a fully human antibody screened from human antibody libraries, but the present invention is not limited thereto.

As used herein, the term "antigen binding fragment" of the anti-TIGIT antibody refers to a fragment having a function capable of binding to an antigen of the anti-TIGIT antibody, that is, TIGIT and encompasses Fab, Fab', F(ab')2, scFv, (scFv)$_2$, scFv-Fc, Fv and the like, which is used interchangeably with "antibody fragment".

Fab includes a variable region of each of the heavy chain and the light chain, a constant region of the light chain, and the first constant region (CH1 domain) of the heavy chain, each having an antigen-binding site. Fab' is different from Fab in that it further has a hinge region including at least one cysteine residue at a C-terminus of the CH1 domain of the heavy chain. F(ab')2 is formed by a disulfide bond between cysteine residues in the hinge region of Fab'.

An Fv (variable fragment) including a variable region of each of the heavy chain and the light chain is the minimal antibody fragment having original specificity of parent immunoglobulin. Double chain Fv (dsFv, disulfide-stabilized Fv) is formed by binding the variable region of the light chain to the variable region of the heavy chain via a disulfide bond. Single chain Fv (scFv) is an Fv wherein the respective variable regions of the heavy chain and the light chain are covalently linked via a peptide linker. These antibody fragments can be obtained by treating the whole antibody with a protease (for example, Fab can be obtained by restriction-cleaving the whole antibody with papain, and the F(ab')$_2$ fragment can be obtained by restriction-cleaving the whole antibody with pepsin) and are preferably constructed by genetic recombination technology (for example, by amplifying a DNA encoding the heavy chain of the antibody or a variable region thereof or a DNA encoding the light chain or a variable region thereof as a template by PCR (polymerase chain reaction) using a pair of primers, and amplifying using a combination of a pair of primers to link DNA encoding a peptide linker and each of both ends thereof to the heavy chain or a variable region thereof and the light chain or a variable region thereof).

In another aspect, the present invention relates to a nucleic acid encoding the anti-TIGIT antibody according to the invention. As used herein, the nucleic acid may be present in a cell or a cell lysate, or in a partially purified form or in a substantially pure form. The nucleic acid may be "isolated" or "substantially pure", when purified from other cellular components or other contaminants, for example, nucleic acids or proteins of other cells, by standard techniques including, for example, alkaline/SDS treatment, CsCl banding, column chromatography, agarose gel electrophoresis and others well-known in the art. The nucleic acid of the present invention may, for example, be DNA or RNA, and may or may not include an intron sequence.

In another aspect, the present invention relates to a vector containing the nucleic acid. For expression of the anti-TIGIT antibody or the antigen-binding fragment thereof according to the present invention, DNA encoding partial- or full-length light and heavy chains is obtained by standard molecular biology techniques (e.g., PCR amplification or cDNA cloning using hybridomas expressing the target antibody), and the DNA may be "operably bound" to transcription and translation control sequences to be inserted into the expression vector.

As used herein, the term "operably bound" may indicate that the gene encoding the antibody is ligated into the vector so that the transcription and translation control sequences can serve the intended function of regulating the transcription and translation of the antibody genes.

The expression vector and expression control sequences which are compatible with the host cell used for expression are selected. The light chain genes of the antibody and the heavy chain genes of the antibody are inserted into separate vectors, or both the genes are inserted into the same expression vector. Antibodies are inserted into expression vectors by standard methods (e.g., ligation of an antibody gene fragment and complementary restriction enzyme sites on vectors, or blunt end ligation when there is no restriction enzyme site). In some cases, the recombinant expression vectors may encode signal peptides that facilitate secretion of the antibody chains from host cells. The antibody chain genes may be cloned into vectors such that signal peptides are attached to the amino terminus of the antibody chain genes in accordance with the frame. The signal peptides may be immunoglobulin signal peptides or heterologous signal peptides (i.e., signal peptides derived from proteins excluding immunoglobulin). In addition, the recombinant expression vectors have regulatory sequences that control the expression of the antibody chain genes in the host cells. "Regulatory sequences" may include promoters, enhancers, and other expression control elements (e.g., polyadenylation signals) that control transcription or translation of the antibody chain genes. It will be appreciated by those skilled in the art that the design of expression vectors can be varied by selecting different regulatory sequences depending on factors such as the choice of host cells to be transformed and the levels of protein expression.

In another aspect, the present invention relates to a host cell containing the nucleic acid or the vector. The host cell according to the present invention is preferably selected from the group consisting of animal cells, plant cells, yeast, *Escherichia coli* and insect cells, but the present invention is not limited thereto.

More specifically, the host cell according to the present invention may be a prokaryotic cell such as *Escherichia coli, Bacillus subtilis, Streptomyces* sp., *Pseudomonas* sp., *Proteus mirabilis,* or *Staphylococcus* sp. In addition, the host cell may be selected from fungi such as *Aspergillus* sp., yeast such as *Pichia pastoris, Saccharomyces cerevisiae, Schizosaccharomyces* sp. or *Neurospora crassa,* and other eukaryotic cells including lower eukaryotic cells, and higher eukaryotic cells derived from insects.

The host cell may also be derived from plants or mammals. Preferably, the host cell is selected from the group consisting of monkey kidney cells (COST), NS0 cells, SP2/0, Chinese hamster ovary (CHO) cells, W138, baby hamster kidney (BHK) cells, MDCK, myeloma cell lines, HuT 78 cells, and HEK293 cells, but the present invention is not limited thereto. Particularly preferably, CHO cells are used.

The nucleic acid or the vector is transformed or transfected into a host cell. Various techniques commonly used to introduce foreign nucleic acids (DNA or RNA) into prokaryotic or eukaryotic host cells for "transformation" or "transfection" include electrophoresis, calcium phosphate precipitation, DEAE-dextran transfection, lipofection or the like. Various expression host/vector combinations may be used to express the anti-TIGIT antibody according to the invention. Suitable expression vectors for eukaryotic hosts include, but are not limited to, expression regulatory sequences derived from SV40, cow papillomavirus, adenovirus, adeno-associated virus, cytomegalovirus and retrovirus. The expression vectors used for bacterial hosts include bacterial plasmids derived from *Escherichia coli* such as pET, pRSET, pBluescript, pGEX2T, pUC vector, col E1, pCR1, pBR322, pMB9 and derivatives thereof, plasmids with a broader host range such as RP4, phage DNAs that can be exemplified by various phage lambda derivatives such as λgt10, λgt11 and NM989, and other DNA phages such as DNA phages of M13 and filamentous single strands. The expression vectors useful for yeast cells are 2° C. plasmids and derivatives thereof. The vector useful for insect cells is pVL941.

In another aspect, the present invention relates to a method for producing the anti-TIGIT antibody or the antigen-binding fragment thereof according to the present invention including culturing host cells to express the anti-TIGIT antibody or the antigen-binding fragment thereof according to the present invention.

When a recombinant expression vector capable of expressing the anti-TIGIT antibody or the antigen-binding fragment thereof is introduced into a mammalian host cell, the antibody can be produced by incubation for a period of time sufficient to allow expression of the antibody in the host cell, more preferably, for a period of time sufficient to allow the antibody to be secreted into a culture medium.

In some cases, the expressed antibody may be separated from the host cells and purified to homogeneity. The separation or purification of the antibody can be carried out by separation and purification methods commonly used for proteins, for example, chromatography. The chromatography may, for example, include affinity chromatography including a protein A column and a protein G column, ion exchange chromatography or hydrophobic chromatography. In addition to the chromatography, the antibody can be separated and purified by a combination of filtration, ultrafiltration, salting out, dialysis or the like.

In another aspect, the present invention relates to a pharmaceutical composition for treating cancer or tumors containing the anti-TIGIT antibody or the antigen-binding fragment thereof as an active ingredient.

In another aspect, the present invention relates to a method for treating cancer or tumors including administering the anti-TIGIT antibody or the antigen-binding fragment thereof to a patient in need of prevention or treatment.

In another aspect, the present invention relates to a use of the anti-TIGIT antibody or the antigen-binding fragment thereof for the treatment of cancer or tumors.

In another aspect, the present invention relates to a use of the anti-TIGIT antibody or the antigen-binding fragment thereof for the preparation of a drug for treating cancer or tumors.

The term "cancer" or "tumor" refers to or means the physiological condition, typically characterized by uncontrolled cell growth/proliferation, of a mammal.

The cancer or carcinoma that can be treated by the composition of the present invention is not particularly limited and includes both solid cancer and blood cancer. Examples of such a cancer include skin cancer such as melanoma, liver cancer, hepatocellular carcinoma, stomach cancer, breast cancer, lung cancer, ovarian cancer, bronchial cancer, nasopharyngeal cancer, laryngeal cancer, pancreatic cancer, bladder cancer, colorectal cancer, colon cancer, cervical cancer, brain cancer, prostate cancer, bone cancer, thyroid cancer, parathyroid cancer, kidney cancer, esophageal cancer, cholangiocarcinoma, testicular cancer, rectal cancer, head and neck cancer, cervical cancer, ureteral cancer, osteosarcoma, neuroblastoma, fibrosarcoma, rhabdomyosarcoma, astrocytoma, neuroblastoma, and glioma, but are not limited thereto. Preferably, the cancer which can be treated by the composition of the present invention is selected from the group consisting of colon cancer, breast cancer, lung cancer and kidney cancer.

The present invention provides a pharmaceutical composition containing a therapeutically effective amount of an anti-TIGIT antibody or an antigen-binding fragment thereof, and a pharmaceutically acceptable carrier. The term "pharmaceutically acceptable carrier" refers to a substance that can be added to the active ingredient to help formulate or stabilize the formulation and does not cause significantly harmful toxic effects on patients.

The carrier refers to a carrier or diluent that does not irritate patients and does not interfere with the biological activities and properties of the administered compound. The pharmaceutical carrier that is acceptable for the composition to be formulated into a liquid solution includes sterile biocompatible ingredients and examples thereof include saline, sterile water, Ringer's solution, buffered saline, albumin injection solutions, dextrose solutions, maltodextrin solutions, glycerol, ethanol and mixtures thereof. If necessary, other conventional additives such as an antioxidant, a buffer and a bacteriostatic agent may be added. In addition, diluents, dispersants, surfactants, binders and lubricants can be additionally added to formulate injectable solutions such as aqueous solutions, suspensions and emulsions, pills, capsules, granules or tablets. Other carriers are described, for example, in [Remington's Pharmaceutical Sciences (E. W. Martin)]. Such a composition may contain a therapeutically effective amount of at least one anti-TIGIT antibody or an antigen-binding fragment thereof.

The pharmaceutically acceptable carrier includes sterile aqueous solutions or dispersions, and sterile powders to prepare sterile injectable solutions or dispersions for extemporaneous application. The use of such media and agents for the pharmaceutical active ingredient is well-known in the art. The composition is preferably formulated for parenteral injection. The composition may be formulated into a solution, microemulsion, liposome, or other ordered structure suitable for high drug concentrations. The carrier may, for example, be a solvent or dispersion medium containing water, ethanol, polyol (such as glycerol, propylene glycol and liquid polyethylene glycol) and a suitable mixture thereof. In some cases, the composition may include isotonic agents, for example, sugars, polyalcohols such as mannitol, sorbitol or sodium chloride. Sterile injectable solutions may be prepared by incorporating a required amount of active ingredient optionally together with one or a combination of the ingredients described above in an appropriate solvent, followed by sterile microfiltration. In general, dispersions are prepared by incorporating the active compound into a sterile vehicle containing a basic dispersion medium and other necessary ingredients selected from those described above. In the case of sterile powders for the preparation of sterile injectable solutions, some preparative methods involve vacuum drying and freeze-drying (lyophilization) to produce powders of the active ingredient and any additional desired ingredient from pre-sterilized and filtered solutions thereof.

The dose of the pharmaceutical composition according to the present invention is not particularly limited, but may be varied depending on various factors including the health condition and weight of patients, the severity of the disease, the type of drugs, administration route and administration time. The pharmaceutical composition according to the present invention may be administered in a single or multiple doses a day to mammals such as rats, mice, domestic animals and humans through a typically acceptable route including, but not limited to, intraperitoneal administration, intravenous administration, intramuscular administration, subcutaneous administration, intradermal administration, oral administration, topical administration, intranasal administration, intrapulmonary administration or intrarectal administration.

The pharmaceutical composition according to the present invention may be administered to a patient in the form of a bolus or by continuous injection, if necessary. For example, bolus administration of the anti-TIGIT antibody or an antigen-binding fragment thereof according to the present invention, presented as a Fab fragment, can be administered at a dose of 0.01 µg/kg body weight to 100 mg/kg body weight, preferably 1 µg/kg body weight to 10 mg/kg body weight.

As used herein, the term "therapeutically effective amount" means an amount of a combination of an anti-TIGIT antibody or an antigen-binding fragment thereof required to cause measurable benefits in vivo in a patient in need of treatment. The exact amount will depend on a number of factors including, but not limited to, the ingredients and physical properties of the therapeutic composition, the population of intended patients and considerations of respective patients and can be readily determined by those skilled in the art. When fully taking these factors into consideration, it is important to administer a minimal amount sufficient to achieve maximum effects without causing adverse effects, and this dose can be easily determined by an expert in the field.

In another aspect, the present invention relates to a method for treating cancer and inhibiting the growth of cancer by administering the anti-TIGIT antibody or the antigen-binding fragment thereof, or the pharmaceutical composition containing the same to a subject in need of treatment.

The anti-TIGIT antibody or the antigen-binding fragment thereof, or the pharmaceutical composition containing the same, according to the present invention can be administered in a pharmaceutically effective amount to treat cancer cells or metastasis thereof, or to inhibit the growth of cancer.

The pharmaceutically effective amount may depend on the type of cancer, the age and weight of patients, the nature and severity of symptoms, the type of current treatment, the number of treatments, administration form and administration route, and can be easily determined by those skilled in the art. The composition of the present invention may be administered simultaneously or sequentially with the aforementioned pharmacological or physiological ingredients, and may be administered in combination with a conventional therapeutic agent, and administered sequentially or simultaneously with a conventional therapeutic agent. Such administration may be single or multiple administration. It is important to administer in a minimal amount capable of achieving the maximum effect without causing side effects in consideration of all of the above factors and, and can be easily determined by those skilled in the art.

As used herein, the term "subject" is intended to mean a mammal, preferably a human, which suffers from or is susceptible to a condition or disease which can be palliated, inhibited or treated by administration of the anti-TIGIT antibody or the antigen-binding fragment thereof or the pharmaceutical composition containing the same.

The anti-TIGIT antibody or the antigen-binding fragment thereof, and the pharmaceutical composition containing the same according to the present invention can be used in combination with a conventional therapeutic agent.

Accordingly, in another aspect, the present invention relates to a composition for co-administration for treating a cancer or tumor containing the anti-TIGIT antibody or the antigen-binding fragment thereof, and other therapeutic agent for cancer, and a method for treating cancer or tumors using the same.

The other therapeutic agent for cancer means any therapeutic agent that can be used for the treatment of cancer, in addition to the anti-TIGIT antibody or the antigen binding fragment thereof according to the present invention.

In the present invention, the therapeutic agent for cancer may be an immune checkpoint inhibitor, but the present invention is not limited thereto.

In the present invention, the immune checkpoint inhibitor is also called "checkpoint inhibitor", and may be an anti-CTLA-4 antibody, an anti-PD-1 antibody or an anti-PD-L1 antibody, but the present invention is not limited thereto. Specifically, the immune checkpoint inhibitor may be ipilimumab, nivolumab, pembrolizumab, atezolizumab, avelumab, durvalumab, or the like, but the present invention is not limited thereto.

The term "use in combination (co-administration)" means that the anti-TIGIT antibody or the antigen-binding fragment thereof and each of the other therapeutic agents for cancer can be administered simultaneously, sequentially or in reverse order, and can be administered as a combination of appropriate effective amounts within the scope that can be conceived by those skilled in the art.

In one embodiment of the present invention, it was confirmed that administration in combination (co-administration) of the anti-PD-L1 antibody and the anti-TIGIT antibody according to the present invention further inhibits the growth of tumors.

The composition for co-administration includes an anti-TIGIT antibody and the configurations associated therewith are the same as those contained in the composition for preventing or treating cancer as described above, such that the description of each configuration applies equally to the composition for co-administration.

In one aspect, the present invention provides an antibody-drug conjugate including a drug conjugated to the anti-TIGIT antibody or the antigen-binding fragment thereof according to the present invention, and a pharmaceutical composition containing the antibody-drug conjugate. The present invention also provides a method for treating tumors using the antibody-drug conjugate including a drug conjugated to an anti-TIGIT antibody or an antigen-binding fragment thereof according to the present invention, and a pharmaceutical composition containing the antibody-drug conjugate.

The anti-TIGIT antibody or the antigen-binding fragment thereof may bind to the drug via a linker. The linker is a site linking the anti-TIGIT antibody or the antigen-binding fragment thereof to a drug. For example, the linker enables the drug to be released from the antibody by cleavage of the linker in the presence of an agent that can be cleaved under intracellular conditions, that is, in an intracellular environment.

The linker may be cleaved by a cleavage agent present in the intracellular environment, such as a lysosome or endosome and may, for example, be a peptide linker that can be cleaved by an intracellular peptidase or a protease such as a lysosome or endosome protease. Generally, a peptide linker has a length of at least two amino acids. The cleavage agent may include cathepsin B and cathepsin D or plasmin and may hydrolyze a peptide to release the drug into the target cells.

The peptide linker may be cleaved by a thiol-dependent protease, cathepsin-B, which is overexpressed in cancer tissues and is, for example, a Phe-Leu or Gly-Phe-Leu-Gly linker. In addition, the peptide linker may, for example, be cleaved by an intracellular protease, which is a Val-Cit linker or a Phe-Lys linker.

In one embodiment, the cleavable linker may be sensitive to pH and may be susceptible to hydrolysis at a certain pH value. Generally, pH-sensitive linkers can be hydrolyzed under acidic conditions. Examples of acid labile linkers, which can be hydrolyzed in lysosomes, include hydrazones, semicarbazones, thiosemicarbazones, cis-aconitic amides, orthoesters, acetals, ketals and the like.

In another embodiment, the linker may be cleaved under reducing conditions, and an example thereof is a disulfide linker. Various disulfide bonds can be formed using N-succinimidyl-S-acetylthioacetate (SATA), N-succinimidyl-3-(2-pyridyldithio) propionate (SPDP), N-succinimidyl-3-(2-pyridyldithio)butyrate (SPDB) and N-succinimidyl-oxycarbonyl-alpha-methyl-alpha-(2-pyridyl-dithio)toluene (SMPT).

The drug and/or drug-linker may be randomly conjugated through the lysine of the antibody or may be conjugated through the exposed cysteine upon reduction of the disulfide bond chain. In some cases, the linker-drug can be conjugated through cysteine present in a genetically engineered tag, e.g., a peptide or protein. The genetically engineered tag, e.g., a peptide or protein, may contain an amino acid motif that can be recognized by, for example, an isoprenoid transferase. The peptide or protein has a deletion at the carboxyl end of the peptide or protein, or an addition through a covalent bond of a spacer unit at the carboxyl (C) end of the peptide or protein.

In addition, the linker may be, for example, a non-cleavable linker and the drug may be released by only one step of antibody hydrolysis to produce, for example, an amino acid-linker-drug complex. This type of linker may be a thioether or maleimidocaproyl group, and remain stable in the blood.

The drug in the antibody-drug conjugate may bind as an agent having a pharmacological effect to an antibody and may specifically be a chemotherapeutic agent, toxin, microRNA (miRNA), siRNA, shRNA or radioisotope. The chemotherapeutic agent may, for example, be a cytotoxic agent or an immunosuppressive agent. Specifically, the drug may contain a microtubulin inhibitor, a mitotic inhibitor, a topoisomerase inhibitor, or a chemotherapeutic agent capable of serving as a DNA intercalator. The drug may also contain an immunomodulatory compound, an anticancer agent and an antiviral agent or a combination thereof.

Such a drug may include one or more selected from the group consisting of maytansinoid, auristatin, aminopterin, actinomycin, bleomycin, thalidomide, camptothecin, N8-acetylspermidine, 1-(2-chloroethyl)-1,2-dimethyl sulfonyl hydrazide, esperamicin, etoposide, 6-mercaptopurine, dolastatin, trichothecene, calicheamicin, taxol, taxane, paclitaxel, docetaxel, methotrexate, vincristine, vinblastine, doxorubicin, melphalan, chlorambucil, duocarmycin, L-asparaginase, mercaptopurine, thioguanine, hydroxyurea, cytarabine, cyclophosphamide, ifosfamide, nitrosourea, cisplatin, carboplatin, mitomycin (mitomycin A, mitomycin C), dacarbazine, procarbazine, topotecan, nitrogen mustard, cytoxan, etoposide, 5-fluorouracil, CNU (bischloroethylnitrosourea), irinotecan, camptothecin, bleomycin, idarubicin, daunorubicin, dactinomycin, plicamycin, mitoxantrone, asparaginase, vinorelbine, chlorambucil, melphalan, carmustine, lomustine, busulfan, treosulfan, dacarbazine, etoposide, teniposide, topotecan, 9-aminocamptothecin, crisnatol, trimetrexate, mycophenolic acid, tiazofurin, ribavirin, EICAR (5-ethynyl-1-beta-Dribofuranosylimidazole-4-carboxamide), hydroxyurea, deferoxamine, floxuridine, doxifluridine, raltitrexed, cytarabine(ara C), cytosine arabinoside, fludarabine, tamoxifen, raloxifene, megestrol, goserelin, leuprolide acetate, flutamide, bicalutamide, EB1089, CB1093, KH1060, verteporfin, phthalocyanine, Pe4 (photosensitizer), demethoxy-hypocrellin A, interferon-α, interferon-γ, tumor necrosis factor, gemcitabine, Velcade, Revlimid, thalomid, lovastatin, 1-methyl-4-phenylpyridiniumion, staurosporine, actinomycin D, dactinomycin, bleomycin A2, bleomycin B2, peplomycin, epirubicin, pirarubicin, zorubicin, verapamil, thapsigargin, nucleases and toxins derived from bacteria or plants and animals, but is not limited thereto.

Hereinafter, the present invention will be described in more detail with reference to the following examples. However, it will be obvious to those skilled in the art that these examples are provided only for illustration of the present invention and should not be construed as limiting the scope of the present invention.

Example 1: Screening of Anti-TIGIT Antibodies 1.1 Screening of Anti-TIGIT Human Antibody scFv and Fab Clones Antibodies specifically binding to TIGIT were selected by a phage display screening method using scFv and Fab human antibody libraries. The scFv library was produced with reference to the description in "Construction of a Large Synthetic Human scFv Library with Six Diversified CDRs and High Functional Diversity (Yang H Y et al Molecules and Cells 27, 225-235)" and the Fab library was produced with reference to the description in Korean Patent No. 1694832. Phage display screening was conducted up to the fourth round in total, and as the number of rounds increased, the amount of antigen decreased and the number of washings increased. An antigen-crossing method was conducted using human TIGIT-ECD-Fc antigens for the first and third phage display screening and using mouse TIGIT-ECD-Fc antigens for the second and fourth phage display screening. 20 μg of a TIGIT antigen diluted in PBS buffer was added to an immune tube and was incubated at 4° C. overnight to coat the surface of the immune tube with the TIGIT antigen. The immune tube coated with the TIGIT antigen was blocked in a PBS-T/BSA (5%) solution for 1 hour at room temperature, scFv or Fab human antibody library phages were added thereto in an amount of $4.7 \times 10^{12}$ or $1.2 \times 10^{13}$, respectively, and the mixture was incubated at room temperature for 2 hours to bind the human antibody library phages to the TIGIT antigens. The phages that did not bind to the TIGIT antigens were removed by washing with PBST (pH 7.4) solution. The residue was eluted with a 0.1 M glycine (pH 3.0) solution and neutralized with a 1M Tris-HCl (pH 8.0) solution. The eluted phages were infected with ER2537 E. coli ($OD_{600}$ of 0.5) at 37° C., amplified with VCSM13 helper phages and used in the next screening round. Results of determination of the number of phages during each panning screening round and of the ratio of the total number of phages and the number of eluted phages showed that the number of phages bound to TIGIT antigens increased with an increasing panning number.

The phage clones obtained from the resulting products of each panning round were infected with ER2537 E. coli strains and seeded on ampicillin plates to obtain colonies. The binding specificity of the colonies to the TIGIT antigens was determined by the following ELISA method using a periplasmic extract. The colonies were seeded by picking in a 96-well plate, in which 120 μL of SB/carbenicillin (50 μg/mL) media was dispensed, and cultured in a 37° C. plate shaker (2 speed) until $OD_{600}$ reached 0.6. 30 μL of SB/carbenicillin (50 μg/mL)/IPTG 5 mM media was added and incubated overnight in a 37° C. plate shaker (2 speed). The sample was centrifuged at 3,000 rpm for 10 minutes to remove the supernatant. The resulting pellet was thoroughly resuspended (dissociated) in 100 μL of BBS solution (200 mM boric acid, 150 mM NaCl, 1 mM EDTA) and incubated at 4° C. for 1 hour. After centrifugation at 3,000 rpm for 20 minutes, only the resulting supernatant was isolated to thus obtain a periplasmic extract. 80 μL of the periplasmic extract was mixed with 80 μL of TBST (5% BSA), followed by blocking at room temperature for 1 hour. The blocked periplasmic extract was added at a dose of 80 µL/well to the 96-well plate coated with human IgG, human TIGIT-Fc and mouse TIGIT-Fc antigens, and incubated at room temperature for 1 hour to bind the antibodies to the antigens. After washing three times with TBST, the TBST (5% BSA) solution diluted at 1:3000 with anti-HA-HRP (Roche) was added at a dose of 30 µL/well to the well and incubated at room temperature for 1 hour. After washing three times with TBST, the TMB solution was added at a dose of 30 µL/well to induce color development. After ceasing the reaction with 1N $H_2SO_4$, absorbance was measured at 450 nm. The antibody clones having binding affinity to TIGIT antigens were screened by ELISA using the antibody periplasmic extracts, and 14 types of antibody clones (S02, S03, S04, S05, S06, S11, S12, S14, S19, S32, S39, S43, S62, S64) were screened for the scFv library and four types of antibody clones (F01, F02, F03, F04) were screened for the Fab library.

1.2 IgG Cloning of Screened scFv and Fab Clones and Production and Purification of Antibodies In order to produce IgG-type antibodies from the screened scFv and Fab clones, each variable region gene was subjected to gene cloning using an expression vector containing the constant region gene of the IgG1 antibody. The variable region genes of the PCR-amplified heavy and light chains from scFv and Fab clones were subjected to cloning using a restriction enzyme of ClaI (NEB), NheI (NEB) or a combination of ClaI and BsiWI (NEB) to produce vectors that can be expressed in the form of IgG. PcDNA3.3 (Invitrogen) vectors were used for heavy chains and pOptiVEC (Invitrogen) vectors were used for light chains. Production of the IgG-type antibodies was carried out by transient transfection using the 293F cell line (Invitrogen). The 293F cells were transfected with the pcDNA3.3 and pOptiVEC vector DNAs cloned in the form of IgG and the cell culture was harvested on the 6th day and was used for purification. Fc purification was performed using Protein A resin to purify antibodies from the antibody culture. The antibody culture was made to flow at a flow rate of 1 mL/min into the MabSelect SuRe Protein A resin (GE Healthcare) equilibrated with 1×PBS (pH 7.4) to induce binding. After completion of binding of the antibody, the resin was primarily washed with 1×PBS (pH 7.4) and then secondarily washed with a 0.1M glycine (pH 5.5) solution. In order to obtain the final antibodies, elution using a 0.1M glycine (pH 3.5) solution and neutralized with 1M Tris-HCl (pH 8.0) solution were performed.

In order to determine the species cross-reactivity of the anti-TIGIT antibodies screened by phage display screening, whether or not the anti-TIGIT antibodies bound to human TIGIT (R&D Systems), mouse TIGIT (R & D Systems) and rhesus TIGIT antigens was identified by ELISA. The rhesus TIGIT antigens used herein were expressed and purified in the form of Fc-fusion by gene synthesis with reference to the Rhesus TIGIT gene sequence (NCBI accession No. XP_014985303.1). Each of three types of the TIGIT antigens diluted at a concentration of 1 mg/mL in PBS was added at 30 µl/well to a 96-well plate and incubated overnight at 4° C. to induce coating. Then, 30 ng of the screened antibody was bound to the TIGIT antigen, and 30 µL of a TBST (5% BSA) solution diluted at 1:3,000 was added to each well and incubated at room temperature for 1 hour. After washing three times with TBST, 30 µL of the TMB solution was added to each well to induce color development. After ceasing the reaction with 1N $H_2SO_4$, color development was determined at an absorbance of 450 nm. The species cross-reactivity of the screened antibodies bound to six types of antigens was identified (FIG. 1). The results showed that most of the antibodies used for the test bound to both human TIGIT and mouse TIGIT.

Figure 2:
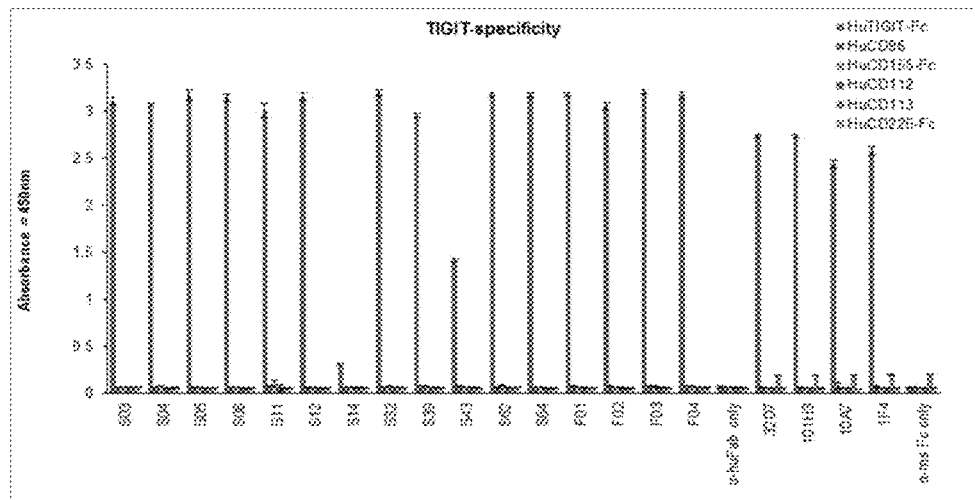
FIG. 2 is a graph showing the results of ELISA to identify binding of anti-TIGIT antibodies to TIGIT, CD96, CD155, CD112, CD113 and CD226 in order to determine specificity of TIGIT superfamilies of the initially selected anti-TIGIT antibodies.

The binding of the anti-TIGIT antibodies to TIGIT superfamilies such as CD96 (Sinobiological), CD155 (Sinobiological), CD112 (R&D Systems), CD113 (R&D Systems) and CD226 (R&D Systems) antigens was identified by ELISA in order to determine the TIGIT specificity of the anti-TIGIT antibodies screened by phage display screening. Six types of antigens including TIGIT were coated at 100 ng/well on a 96-well plate, treated with 30 ng of each screened antibody and incubated at room temperature for 1 hour. After washing three times with TBST, 30 µL of TBST (5% BSA) diluted at 1:3,000 with an anti-human Fab-HRP secondary antibody (Jackson) was added to each well and incubated at room temperature for 1 hour. After washing three times with TBST, 30 µL of the resulting TMB solution was added to each well. After ceasing the reaction with 1N $H_2SO_4$, color development was determined at an absorbance of 450 nm. The binding of the selected antibodies to the six antigens was identified. As a result, it can be seen that all the antibodies specifically bound only to the TIGIT antigen (FIG. 2).

Figure 3:
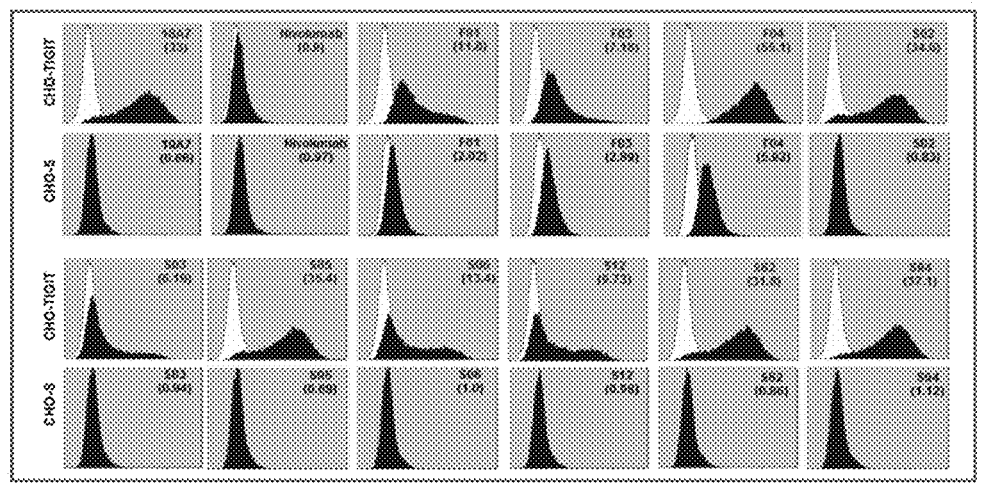
FIG. 3 shows the results of measurement using a fluorescence flow cytometer in order to identify binding of the initially selected anti-TIGIT antibodies to TIGIT antigens expressed on the cell surface.

Finally, FACS analysis was carried out using a CHO-S cell line (CHO-hTIGIT) overexpressing human TIGIT proteins in order to identify binding of the screened antibodies to the TIGIT antigens expressed on the cell surface. The CHO-S cell line (CHO-hTIGIT) was produced by transducing full-length human TIGIT gene CHO-S cells using a lentiviral vector, followed by screening of only CHO cells overexpressing human TIGIT with antibiotic blasticidin. The produced CHO-hTIGIT cell line was washed with ice-cold PBS, and $5 \times 10^4$ cells were transferred to a tube, treated with 1 µg of each IgG-produced antibody and incubated on ice for 1 hour. Subsequently, the cell line was treated with 1 µg of an anti-human IgG FITC secondary antibody (Invitrogen) and incubated on ice for 1 hour. The cells were washed with ice-cold PBS and then subjected to FACS analysis to identify binding of the antibodies to the human TIGIT antigens expressed on the cell surface (FIG. 3). The 10A7 antibodies used as a positive control were hamster-derived anti-human antibodies allowing for mouse cross-linking, and a variable region was produced by the present inventors by producing genes in the form of an antibody having a constant region of mouse IgG2a, based on the sequence described in US Patent No. 2015/0216970. The 10A7 antibody bound to the human TIGIT antigen, but did not bind to nivolumab (anti-PD1 antibody) used as a negative control. This means that the CHO-hTIGIT cells were normally produced. The screened antibodies were identified to specifically bind to the CHO-hTIGIT cells.

Example 2. Optimization of Anti-TIGIT Antibodies 2.1 Optimization of F04 and S64 Antibodies Two types of clones, F04 and S64, were finally screened as anti-TIGIT human antibodies through the antibody screening process described above. In order to improve the stability of these antibodies, sub-libraries were constructed, based on the amino acid sequences of the F04 and S64 antibodies, and screening to improve stability was performed at a high temperature using an extended washing method. The sub-library of the F04 antibody was a library obtained by simultaneously shuffling CDRH1 and CDRH2, which was prepared by overlapping one species. Three types of sub-libraries including the library obtained by simultaneously shuffling CDRH1 and CDRH2, the library obtained by simultaneously shuffling CDRL1, CDRL2 and CDRL3, and the library obtained by shuffling other CDRs, excluding CDRH3, were produced by an overlapping PCR method. The CDR regions that had amino acid sequence diversity for F04 and S64 clonal optimization are shown in Table 5 below (CDR region is underlined).

TABLE 5

Variable region sequences of F04 and S64

| Clone | | |
|---|---|---|
| F04 | Heavy chain | EVQLLESGGGLVQPGGSLRLSCAASGFTFSSYYMSWVRQAP GKGLEWVSSIGSYYTYYADSVKGRFTISRDNSKNTLYLQMN SLRAEDTAVYYCARSSYSGGNGYYYYAYAFDYWGQGTLVT VSS (SEQ ID NO: 17) |
| | Light chain | EIVLTQSPGTLSLSPGERATLSCRASQSVSSSYLAWYQQKPGQ APRLLIYGASSRATGIPDRFSGSGSGTDFTLTISRLEPEDFAVY YCQQGYHRYATFGQGTKVEIK (SEQ ID NO: 18) |
| S64 | Heavy chain | EVQLLESGGGLVQPGGSLRLSCAASGFTFSNYAMSWVRQAP GKGLEWVSAIYPGGGSIYYADSVKGRFTISRDNSKNTLYLQM NSLRAEDTAVYYCAKAIRTCSLSHCYYYYGMDVWGQGTLV TVSS (SEQ ID NO: 19) |
| | Light chain | QSVLTQPPSASGTPGQRVTISCSCSSSNIGNNAVSWYQQLPGT APKLLIYDSNRPSGVPDRFSGSKSGTSASLAISGLRSEDEAD YYCGSWDYSLSAYVFGGGTKLTVLG (SEQ ID NO: 20) |

The phages were rescued from the sub-library that had been constructed in order to screen clones that were more stable than the parental clones and were then heated before binding to the antigens to remove unstable clones. In the first and second phage display screenings, the phages were treated at 60° C. for 10 minutes, and in the third to sixth phage display screenings, the phages were treated at 80° C. for 10 minutes. In addition, during ELISA, screening was conducted at a remaining ratio induced to distinguish clones with improved stability from the parent clones for an increased washing time of 2 hours and at an elevated temperature of 37° C. Based on this, clones with improved stability were screened and sequences thereof were analyzed (Tables 6 and 7).

TABLE 6

CDR sequences of antibodies screened based on F04 clones

| Clone | CDRH1 | CDRH2 | CDRH3 | CDRL1 | CDRL2 | CDRL3 |
|---|---|---|---|---|---|---|
| F04-1 | GYYMS | SIGSYYTYYADSVKG | SSYSGGNGYYYYAYAFDY | RASQSVSSSYLA | GASSRAT | QQGYHRYAT |
| F04-2 | GYYMS | SIGSYYSTYYADSVKG | SSYSGGNGYYYYAYAFDY | RASQSVSSSYLA | GASSRAT | QQGYHRYAT |
| F04-3 | YYYMS | SIGSSYSTYYADSVKG | SSYSGGNGYYYYAYAFDY | RASQSVSSSYLA | GASSRAT | QQGYHRYAT |
| F04-4 | SYYMS | SIGGYSYTYYADSVKG | SSYSGGNGYYYYAYAFDY | RASQSVSSSYLA | GASSRAT | QQGYHRYAT |
| F04-5 | GYYMS | SIGSSYYTYYADSVKG | SSYSGGNGYYYYAYAFDY | RASQSVSSSYLA | GASSRAT | QQGYHRYAT |
| F04-6 | SYYMS | SIGSYSSTYYADSVKG | SSYSGGNGYYYYAYAFDY | RASQSVSSSYLA | GASSRAT | QQGYHRYAT |
| F04-7 | SYYMS | SIGYGSGYTYYADSVKG | SSYSGGNGYYYYAYAFDY | RASQSVSSSYLA | GASSRAT | QQGYHRYAT |
| F04-8 | GYYMS | SIGYGSGYTYYADSVKG | SSYSGGNGYYYYAYAFDY | RASQSVSSSYLA | GASSRAT | QQGYHRYAT |
| F04-9 | YYYMS | SIGGGSSYTYYADSVKG | SSYSGGNGYYYYAYAFDY | RASQSVSSSYLA | GASSRAT | QQGYHRYAT |
| F04-10 | SYYMS | SIGSGSPSTYYADSVKG | SSYSGGNGYYYYAYAFDY | RASQSVSSSYLA | GASSRAT | QQGYHRYAT |

TABLE 7

CDR sequences of antibodies screened based on scFv clones

| Clone | CDRH1 | CDRH2 | CDRH3 | CDRL1 | CDRL2 | CDRL3 |
|---|---|---|---|---|---|---|
| S64-1 | NYAMS | SISPSSGSTYYADSVKG | AIRTCSLSHCYYYYGMDV | SCSSSNIGNNAVS | YDSNRPS | GSWDYSLSAYV |
| S64-2 | NYAMS | AISPGSGNTYYADSVKG | AIRTCSLSHCYYYYGMDV | SCSSSNIGNNAVS | YDSNRPS | GSWDYSLSAYV |
| S64-3 | NYAMS | GIYPSGGNTYYADSVKG | AIRTCSLSHCYYYYGMDV | SGFSSNIGNNAVN | YDNKRPS | GTWDYSLSAYV |
| S64-5 | DYAMN | SIYPNGGSKYYADSVKG | AIRTCSLSHCYYYYGMDV | SCSSSNIGNNAVS | YDSNRPS | GSWDYSLSAYV |
| S64-6 | DYAMS | LIYPSGGSKYYADSVKG | AIRTCSLSHCYYYYGMDV | TGSSSNIGSNYVS | ADSQRPS | GTWDYSLNGYV |
| S64-9 | DYAMS | LIYPSGGSKYYADSVKG | AIRTCSLSHCYYYYGMDV | SGSSSNIGNNYVS | ADNNRPS | GTWDSSLSAYV |
| S64-14 | DYAMS | SIYPSGGSKYYADSVKG | AIRTCSLSHCYYYYGMDV | TGSSSNIGSNYVS | ADSHRPS | GAWDASLSAYV |
| S64-39 | NYAMS | GISPSGSSIYYADSVQG | AIRTCSLSHCYYYYGMDV | SSSSSNIGSNAVN | YDNQRPS | ATWDYSLSGYV |
| S64-56 | NYSMS | GIYPSGGSTYYADSVKG | AIRTCSLSHCYYYYGMDV | SGSSSNIGSNTFN | YDSNRPS | GTWDYSLNGYV |
| S64-65 | NYAMS | SIYPNGGSKYYADSVKG | AIRTCSLSHCYYYYGMDV | SSSSSNIGSNYVS | ADSQRPS | GAWDYSLNAYV |
| S64-73 | NYAMS | WISPSSGSIYYADSVQG | AIRTCSLSHCYYYYGMDV | SCSSSNIGNNAVS | YDSNRPS | GSWDYSLSAYV |
| S64-80 | NYAMS | LIYPSGGSKYYADSVKG | AIRTCSLSHCYYYYGMDV | SGSSSNIGSNYVS | ADSNRPS | GAWDSILIAYV |

Finally, F04-10 clones were screened by screening using the F04 sub-library, and S64-39 clones were screened by screening using the S64 sub-library.

The antibody based on the F04-10 clones includes the amino acid sequence set forth in SEQ ID NO: 13 as the heavy chain variable region and the amino acid sequence set forth in SEQ ID NO: 15 as the light chain variable region, and the antibody based on the S64-39 clones includes the amino acid set forth in SEQ ID NO: 14 as the heavy chain variable region and the amino acid sequence set forth in SEQ ID NO: 16 as the light chain variable region.

In addition, the antibody based on the F04-10 clones includes: a heavy chain variable region including a heavy chain CDR1 including the amino acid sequence set forth in SEQ ID NO: 1; a heavy chain CDR2 including the amino acid sequence set forth in SEQ ID NO: 3; and a heavy chain CDR3 including the amino acid sequence set forth in SEQ ID NO: 5; and a light chain variable region including a light chain CDR1 including the amino acid sequence set forth in SEQ ID NO: 7; a light chain CDR2 including the amino acid sequence set forth in SEQ ID NO: 9; and a light chain CDR3 including the amino acid sequence set forth in SEQ ID NO: 11.

In addition, the antibody based on the S64-39 clones includes: a heavy chain variable region including a heavy chain CDR1 including the amino acid sequence set forth in SEQ ID NO: 2; a heavy chain CDR2 including the amino acid sequence set forth in SEQ ID NO: 4; and a heavy chain CDR3 including the amino acid sequence set forth in SEQ ID NO: 6; and a light chain variable region including a light chain CDR1 including the amino acid sequence set forth in SEQ ID NO: 8; a light chain CDR2 including the amino acid sequence set forth in SEQ ID NO: 10; and a light chain CDR3 including the amino acid sequence set forth in SEQ ID NO: 12.

2.2 Gene Cloning of Anti-TIGIT Antibodies and Purification of Antibodies

The expression vectors of the F04-10-IgG1 and S64-39-IgG1 antibodies were produced in the same manner as in Example 1.2. The heavy chain expression vectors of the S64-39-IgG4 antibodies were produced as follows. The genes corresponding to the IgG1 constant region were removed from the S64-39-IgG1 expression vectors using NheI and XhoI (NEB) restriction enzymes, and genes in which the heavy chain constant region of the anti-PD-1 antibody, nivolumab was treated with NheI and XhoI, were subcloned and then added thereto to produce heavy chain expression vectors such that the S64-39 heavy chains were finally expressed in the form of IgG4. The light chain variable regions of the F04-10 and S64-39 antibodies were subcloned into the pOptiVEC vectors using ClaI and XhoI restriction enzymes, respectively.

Production and purification of the three types of antibodies produced in the form of IgG were carried out using transient expression using a 293F cell line and MabSelect SuRe protein A resin in the same manner as in Example 1.2 above.

Example 3. Test for Identifying Binding of Anti-TIGIT Antibodies to TIGIT on Cell Surface In order to identify the binding ability of the three types of anti-TIGIT antibodies produced in Example 2 to TIGIT expressed on the cell surface, TIGIT-overexpressing CHO cell line (hereinafter referred to as CHO-TIGIT cell line) was treated with anti-TIGIT antibodies and then the anti-TIGIT antibodies bound to TIGIT on the cell surface were detected using a fluorescence flow cytometer.

Figure 4:
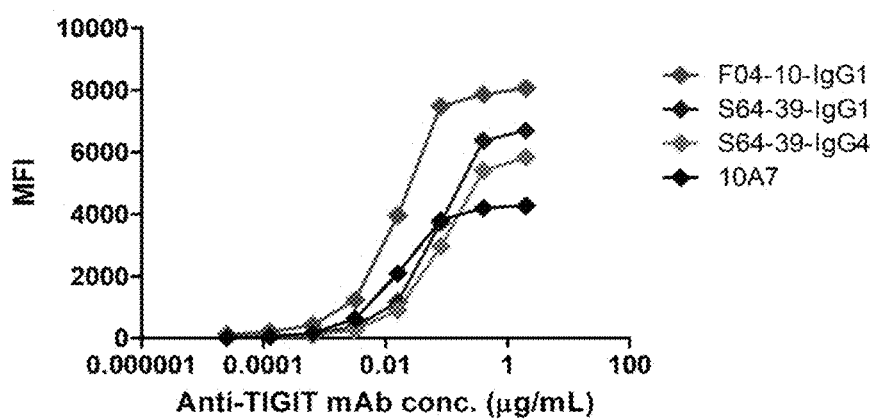
FIG. 4 shows the results of measurement of the degree of binding of anti-TIGIT antibodies to TIGIT proteins on the cell surface using a fluorescence flow cytometer.

Specifically, the CHO-TIGIT cell line was cultured in a 5% CO2 incubator at 37° C. for 48 to 72 hours using a chemical composition medium (CD FortiCHO Chemically Defined Medium+8 mM L-Glutamine+20 µg/mL Blasticidin+1% Anti-clumping agent). The cultured CHO-TIGIT cell line was harvested by centrifugation, diluted in FACS solution (PBS+5% FBS), and dispensed at a density of $1 \times 10^5$ cells/well in a 96-well round bottom plate (Corning). Then, in order to completely remove the chemical composition medium remaining on the cell surface, the FACS solution was added, centrifuged at 2,000 rpm for 3 minutes and washed three times to remove the supernatant. The washed CHO-TIGIT cell line was re-suspended by addition of 100 µL of FACS solution. The anti-TIGIT antibody of each concentration, which was diluted to 2 times the final concentration using the FACS solution, was added at 100 µL to a 96-well round bottom plate in which the CHO-TIGIT cell line was dispensed, and incubated at 4° C. for 1 hour. Then, in order to remove the anti-TIGIT antibody remaining in the supernatant, without binding to the TIGIT on the cell surface, the FACS solution was added to each well, centrifuged at 2,000 rpm for 3 minutes, and washed three times to remove the supernatant. Then, in order to detect anti-TIGIT antibody bound to TIGIT on the cell surface, a goat anti-human IgG (H+L) cross-adsorbed secondary antibody (Invitrogen) was diluted to 10 µg/mL using a FACS solution, and 100 µL of the diluted antibody was incubated at 4° C. for 1 hour. After washing three times, each sample was transferred to a 12×75 mm tube (BD Biosciences) and analyzed using a fluorescence flow cytometer. As a result, it was identified that the binding ability ($EC_{50}$) of the anti-TIGIT antibody to the TIGIT on the cell surface was 16.41 ng/mL for F04-10-IgG1, 69.01 ng/mL for S64-39-IgG1, 80.78 ng/mL for S64-39-IgG4, and 16.54 ng/mL for 10A7 (FIG. 4).

Example 4. Test for Inhibition of Anti-TIGIT Antibody on TIGIT/CD155 Binding In order to identify the activity of the three types of anti-TIGIT antibodies produced in Example 2 above, inhibition of binding between TIGIT and CD155 was tested.

Specifically, in this test, inhibitory activity of the anti-TIGIT antibody on binding between TIGIT and CD155 was carried out in a co-culture system of a CD155-expressing aAPC/CHO-K1 cell line and a TIGIT-expressing effector cell line using a TIGIT/CD155 blockade assay kit (Promega).

Figure 5:
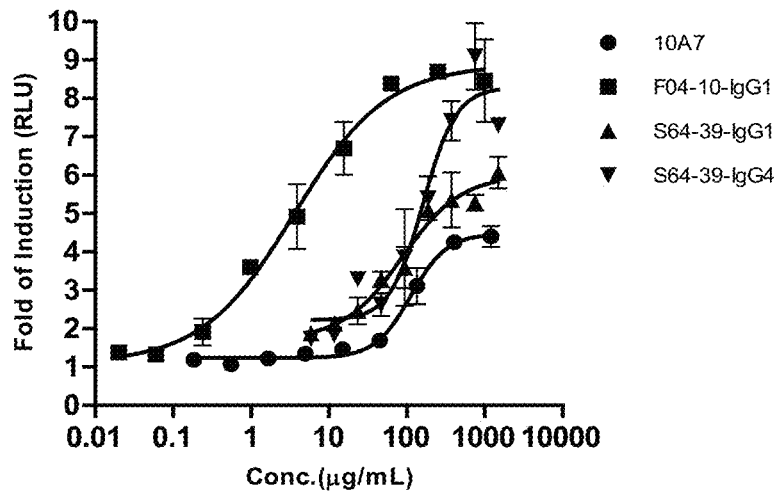
FIG. 5 shows the results of a blockade assay identifying the degree of inhibition on binding between TIGIT and CD155 by treatment with anti-TIGIT antibodies.

A CD155-expressing aAPC/CHO-K1 cell line was dissolved and diluted in 14.5 mL of a basic medium (F-12 medium containing 10% FBS), and 100 µL of the resulting cell line was added to a 96-well plate (Costar) and stored in a CO2 incubator for 16 to 24 hours. For F04-10-IgG1, a concentrate containing the anti-TIGIT antibody was serially diluted 4-fold at 2 mg/mL, which was twice as high as the treatment concentration, using an analytical medium (RPMI 1640 medium containing 10% FBS), and 564-39-IgG1 and 564-39-IgG4 were prepared by 2-fold serial dilutions at 3 mg/mL. The 10A7 antibody used as a control was prepared by 3-fold serial dilution at 2.4 mg/mL. The medium of the 96-well plate containing the CD155-expressing aAPC/CHO-K1 cell line was completely removed, and the prepared anti-TIGIT antibody was added at 40 µL to each well to adjust the actual concentration as follows: for F04-10-IgG1, the sample serially diluted 4-fold at 1 mg/mL was used for treatment, and for 564-39-IgG1 and S64-39 IgG4, the samples serially diluted 2-fold at 1 mg/mL were used for treatment. For the control, 10A7, the sample serially diluted 3-fold at 1.2 mg/mL was used for treatment. Then, the TIGIT-expressing effector cell line was dissolved and diluted in 6 mL of an analytical medium, and 40 µL of the diluted cell line was added to each well, followed by incubation at 37° C. in a 5% CO2 incubator for 6 hours. Each well was treated with 80 µL of the Bio-Glo™ reagent prepared by adding Bio-Glo™ buffer to a Bio-Glo™ substrate and reacted at room temperature for 10 minutes. The response value (relative luminometer units, RLU) was measured with a luminescence-measurable microplate reader (Molecular devices, SpectraMax L) to calculate the ratio of response values (Fold response=$RLU_{Abdilution}/RLU_{noantibodycontrol}$), which means a ratio of response value upon treatment with an anti-TIGIT antibody with respect to response value upon non-treatment with an anti-TIGIT antibody. Results are as follows: The binding inhibition ($EC_{50}$) of the anti-TIGIT antibody was 23.89 nM for F04-10-IgG1, 0.581 µM for S64-39-IgG1, 1.08 µM for S64-39-IgG4 and 0.752 µM for 10A7 (FIG. 5).

Example 5. Test for NK Cell Activation of Anti-TIGIT Antibodies

In order to analyze the activity of the NK92 cell line upon treatment with the three types of anti-TIGIT antibodies produced in Example 2, the amount of IFN-g secretion in the NK92 cell line was measured and the test for identifying NKG2D expression was performed using a fluorescence flow cytometer under the condition of co-culture of the TIGIT-overexpressing NK92 cell line and PVR-overexpressing human-derived ovarian cancer cell line (HeLa cell line).

Specifically, the TIGIT-overexpressing NK92 cell line was diluted to a concentration of $2 \times 10^5$/mL in a complete medium (Alpha-MEM+12.5% FBS+12.5% horse serum+0.1 mM 2-mercaptoethanol+100 U/mL IL-2) and then cultured in a T25 flask (Corning) at a volume of 5 mL at 37° C. in a 5% CO2 incubator for 16 to 24 hours. The cells were treated with 25 µg/mL of an anti-TIGIT antibody to inhibit the overexpressed TIGIT in the cultured NK92 cell line and cultured at 37° C. in a 5% CO2 incubator for 72 hours.

During the culture of the NK92 cell line and the anti-TIGIT antibody, the PVL-overexpressing HeLa cell line was dissolved and cultured in complete medium (RPMI1640 medium supplemented with 10% FBS) at a concentration of $3 \times 10^5$/mL at a volume of 15 mL in a T75 flask (Corning) and cultured in a 5% CO2 incubator at 37° C. for 24 to 48 hours. Then, the NK92 cell line and the HeLa cell line were co-cultured for 4 to 6 hours at 37° C. in a 5% CO2 incubator at a volume of 1 mL in a 12-well plate (Corning) in a ratio of 1:10 ($1 \times 10^5$ NK92: $1 \times 10^6$ HeLa). After completion of the co-culture, the culture supernatant was obtained and stored at −20° C. for the IFN-g ELISA test, and the cultured cells were diluted in PBS (Gibco) for preparation.

Figure 6:
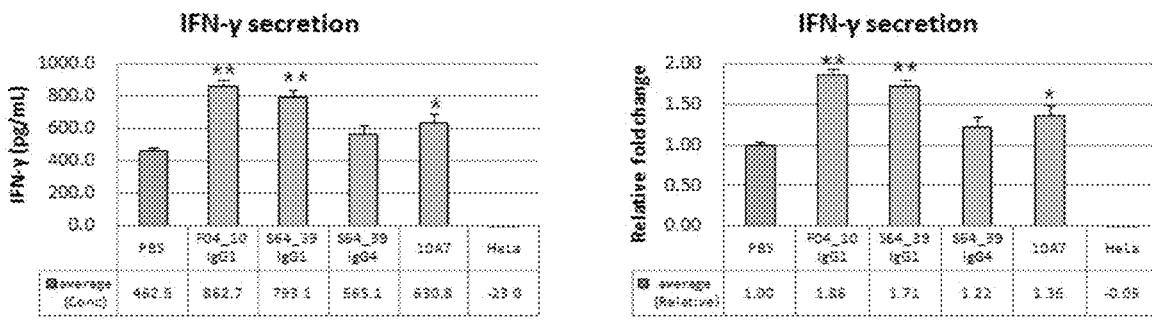
FIG. 6 shows the amount of IFN-g secreted from a NK92 cell line according to treatment with the anti-TIGIT antibody in a co-culture of the NK92 cell line overexpressing TIGIT and a HeLa cell line overexpressing PVR.

Using the culture supernatant and cell line obtained through the above procedure, First, an ELISA test was conducted to determine the amount of IFN-g secreted from the NK92 cell line using the culture supernatant. This test was performed using a human IFN-gamma Qantikine ELISA assay kit (R&D systems). From results of analysis of the amount of IFN-g secreted from NK92 cells upon treatment with the anti-TIGIT antibody, it can be seen that groups treated with F04-10-IgG1 and S64-39-IgG1 antibodies exhibited a significant increase in IFN-g secretion, as compared to the group treated with the control antibody, and the group treated with the 564-39-IgG4 antibody had a level of IFN-g secretion equivalent to that of the group treated with the control antibody (FIG. 6).

Figure 7:
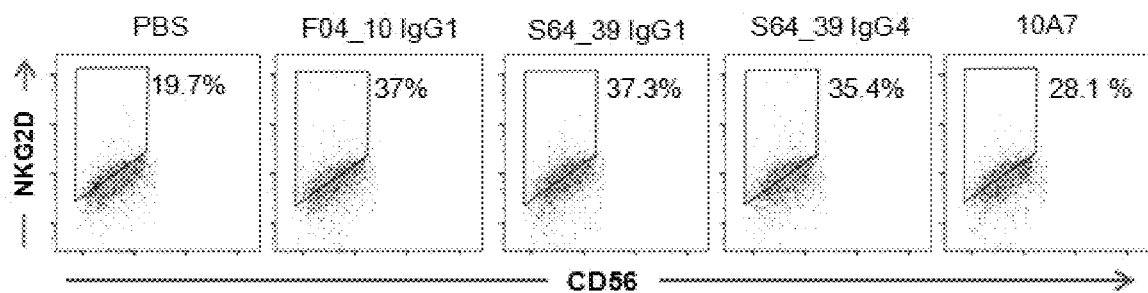
FIG. 7 shows the results of measurement of NKG2D expression in a NK92 cell line by treatment with the anti-TIGIT antibody using a fluorescence flow cytometer under the condition of co-culture of the NK92 cell line overexpressing TIGIT and the HeLa cell line overexpressing PVR.

Secondly, the present inventors conducted analysis using a fluorescence flow cytometer to identify the expression of NKG2D, one of the NK cell activation marker proteins for the cell line obtained by the aforementioned co-culture. For immunostaining of cell lines, first, the cell lines were diluted at a concentration of $1 \times 10^6$/mL in a cell staining buffer (Biolegend) and eFluor-anti-CD56 antibody (eBioscience) staining and PE-anti-NKG2D antibody (BD Biosciences) staining were conducted at 4° C. for 20 minutes in the absence of light to specifically isolate only NK92 cells. Then, in order to clean the stains, 1 mL of a cell staining buffer was added and centrifuged at 2,000 rpm for 5 minutes, and this operation was repeated three times. Then, each sample was transferred to a 12×75 mm tube for fluorescent flow cytometry (BD Biosciences), and the expression pattern of NKG2D was identified in a cell line expressing CD56 using a fluorescence flow cytometer. As a result, it was identified that NKG2D expression was significantly increased in the F04-10-IgG1, S64-39-IgG1 and S64-39-IgG4 antibody-treated groups, as compared to the control antibody-treated group (FIG. 7).

Example 6. Test for Measurement of Affinity of Anti-TIGIT Antibodies to TIGIT Antigens In order to measure binding abilities of the three types of anti-TIGIT antibodies produced in Example 2 to human TIGIT (rhTIGIT-Fc) and mouse TIGIT (rmTIGIT-Fc), surface plasmon resonance (SPR) using a BIAcore T200 (GE Healthcare) was used. The SPR method is based on the principle that the refractive index of light passing through a sensor chip changes according to the state of a substance coated on the sensor chip. When an antigen or antibody was made to flow into the chip coated with the antigen or antibody, the refractive index is changed due to binding therebetween and the affinity ($K_D$) value is calculated from the measured value.

An anti-TIGIT antibody was immobilized on a Series S CM5 sensor chip (GE Healthcare) to a level of 500 RU using a 10 mM acetate solution (pH 4.0) and an amine coupling kit (GE Healthcare). Human or mouse TIGIT-Fc (R&D Systems) proteins were serially diluted 2-fold from a concentration of 40 nM in HBS-EP buffer (0.01M HEPES, pH 7.4, 0.15 M NaCl, 3 mM EDTA, 0.005% surfactant P20, GE Healthcare) and were each flowed to measure the antigen-antibody affinity while inducing association, dissociation, and regeneration with the antibody immobilized on the sensor chip. The association of the TIGIT-Fc proteins was measured at a rate of 30 μL/min for 600 seconds, the dissociation was measured for 2,000 seconds, and the regeneration was carried out in a 10 mM glycine solution (pH 1.5) at a rate of 100 μL/min for 25 seconds. Measurement results of the binding ability to rhTIGIT-Fc and rmTIGIT-Fc are shown in Tables 8 and 9 below.

TABLE 8

Measurement results of binding ability to rhTIGIT-Fc

| Antibody name | On rate (1/Ms) | Off rate (1/s) | Affinity ($K_D$, nM) |
|---|---|---|---|
| F04-10-IgG1 | $7.052 \times 10^4$ | $3.760 \times 10^{-5}$ | 0.533 |
| S64-39-IgG1 | $3.366 \times 10^4$ | $4.414 \times 10^{-5}$ | 1.311 |
| S64-39-IgG4 | $2.821 \times 10^4$ | $3.232 \times 10^{-5}$ | 1.146 |
| 10A7 | $1.624 \times 10^5$ | $1.927 \times 10^{-4}$ | 1.187 |

TABLE 9

Measurement results of binding ability to rmTIGIT-Fc

| Antibody name | On rate (1/Ms) | Off rate (1/s) | Affinity ($K_D$, nM) |
|---|---|---|---|
| F04-10-IgG1 | $1.196 \times 10^5$ | $2.933 \times 10^{-5}$ | 0.245 |
| S64-39-IgG1 | $6.283 \times 10^4$ | $2.008 \times 10^{-4}$ | 3.196 |
| S64-39-IgG4 | $6.218 \times 10^4$ | $1.942 \times 10^{-4}$ | 3.123 |
| 10A7 | $4.904 \times 10^5$ | $8.913 \times 10^{-5}$ | 0.182 |

Example 7. Inhibitory Effect of Anti-TIGIT Antibody on Tumor Growth

In order to evaluate the in vivo activity of the anti-TIGIT antibody, a mouse tumor model (syngeneic CT26 colorectal carcinoma model using BALB/c mice) was prepared. Here, the positive control antibody (10A7) and three type of antibodies (F04-10-IgG1, S64-39-IgG1, S64-39-IgG4) produced in Example 2 were administered alone or in combination with the anti-PD-L1 antibody (10F.9G2-rat IgG2b) and inhibition effects on tumor growth were comparatively evaluated therebetween.

First, in order to establish the mouse tumor model, cultured CT26 tumor cells were subcutaneously implanted (Day 0) by injection at a dose of 100 μL ($1 \times 10^6$ cells)/mouse, and the tumor was allowed to grow to exceed a certain size. After 8 days, when the tumor volume reached 119 mm³ (Day 8, administration start day), a negative control (rat IgG2b, dose of 10 mg/kg) and four test substances (dose of 25 mg/kg) were administered intraperitoneally three times in total at intervals of 3 days in combination with the anti-PD-L1 antibody (dose of 10 mg/kg). The tumor volume and body weight were then measured at intervals of 2 weeks. The inhibitory effect on tumor growth was expressed as TGI calculated by applying the tumor volume measured on the final day of the in vivo test (Day 28) to the following formula:

$$TGI\ rate\ (\%) = 100 \times (1 - \Delta T / \Delta C)$$

Figure 8:
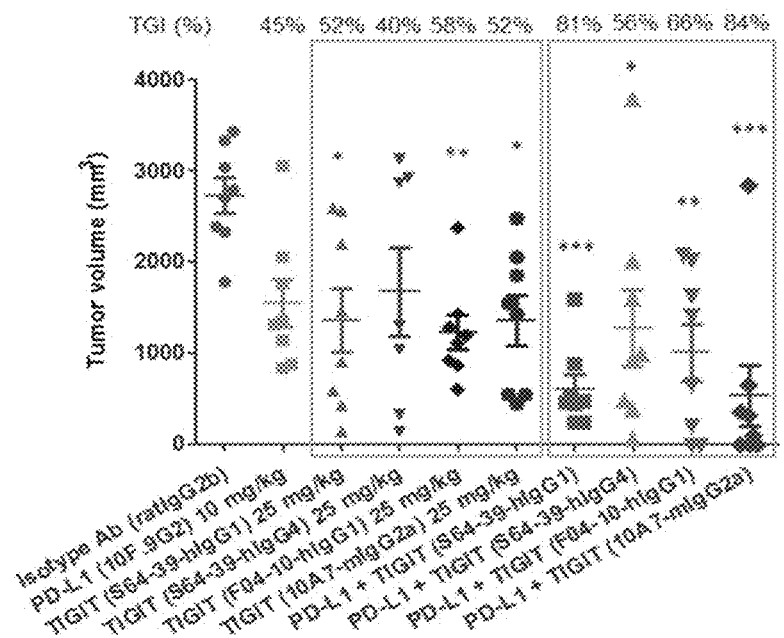
FIG. 8 is a graph showing a tumor volume on the final day of a test to evaluate in vivo efficacy of the anti-TIGIT antibody according to one embodiment and showing results indicating efficacy in a CT26 tumor model.

ΔT=Mean tumor volume of test substance-administered group measured on the final day−mean tumor volume of test substance-administered group measured on the administration start day Δc=Mean tumor volume of negative control-administered group measured on the final day−mean tumor volume of negative control-administered group measured on the administration start day Tumor volume increased approximately 23-fold on the final day in the negative control-administered group, as compared to the administration start day. As compared with the negative control, the positive control antibody and the anti-PD-L1 antibody showed a moderate anti-tumor effect when administered alone and administration of a combination of the two antibodies showed a stronger and significant tumor inhibition effect (FIG. 8). In the case of the anti-TIGIT antibodies, two kinds of IgG1-type antibodies (S64-39-IgG1, F04-10-IgG1) showed an effect similar to that of the positive control antibody when administered alone and S64-39-IgG1 showed an equivalent level of effect when administered in combination. The S64-39-IgG4 antibody had a slightly lower effect than S64-39-IgG1, when administered alone and in combination.

In conclusion, the three kinds of antibodies (F04-10-IgG1, S64-39-IgG1, S64-39-IgG4) produced in Example 2 above had a significant anti-tumor effect as compared to the negative control-administrated group, when administered alone or in combination with the anti-PD-L1 antibody (F04-10-IgG1, S64-39-IgG1). In particular, when administered alone, two kinds of antibodies (F04-10-IgG1, S64-39-IgG1) had an equivalent anti-tumor effect than the negative control-administrated group, and when administered in combination, one kind of antibody (S64-39-IgG1) had an equivalent anti-tumor effect than the negative control-administrated group.

The statistical analysis shown in FIG. 8 was carried out by Dunnett's multiple comparison using GraphPad Prism 5, and the statistical significance of the difference with respect to the negative control-administrated group was expressed as follows. *: $p<0.05$, : $p<0.01$ and *: $p<0.001$ Example 9. Tumor Growth Inhibitory Effect of Anti-TIGIT Antibody Depending on Dose and Use in Combination In order to evaluate the in vivo activity of the anti-TIGIT antibody depending on dose and use in combination, a mouse tumor model (syngeneic CT26 colorectal carcinoma model using BALB/c mice) was prepared. The antibody F04-10 produced in Example 2 was administered alone or in combination with the anti-PD-L1 antibody (10F.9G2-rat IgG2b) to the mouse tumor model to comparatively evaluate the tumor growth inhibitory effect.

First, in order to establish the mouse tumor model, cultured CT26 tumor cells were subcutaneously implanted (Day 0) by injection at a dose of 100 μL ($1\times10^6$ cells)/mouse, and the tumor was allowed to grow to exceed a certain size. After 7 days, when the tumor volume reached 80 mm³ (day 7, on the administration start day), the test groups were randomly divided into groups with a similar mean tumor volume, and negative control (a combination of rat IgG2b 10 mg/kg and human IgG1 25 mg/kg) or F04-10 (5, 10, 25 mg/kg) was administered intraperitoneally alone or in combination with an anti-PD-L1 antibody at intervals of 3 days three times in total. The tumor volume and body weight were then measured at intervals of 2 weeks. The inhibitory effect on tumor growth was expressed as TGI, calculated by applying the tumor volume measured on the final day of the in vivo test (Day 24) to the following formula:

$$TGI\ rate\ (\%) = 100 \times (1 - \Delta T/\Delta C)$$

Figure 9:
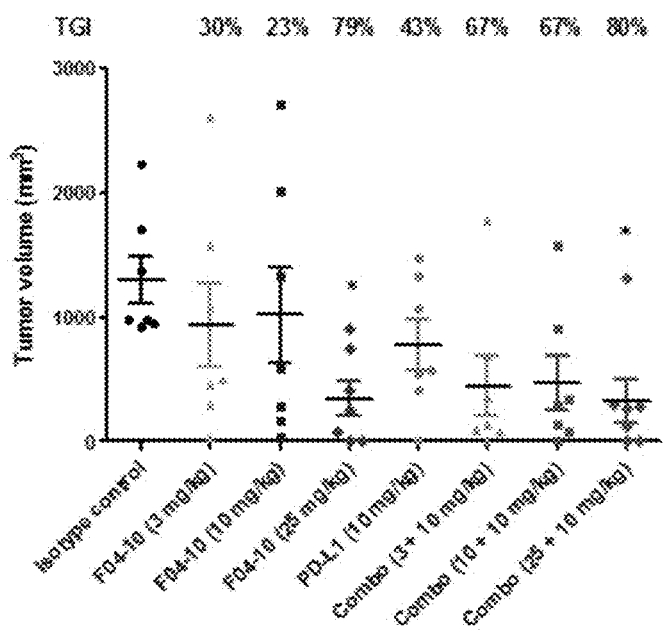
FIG. 9 is a graph showing a tumor volume on the final day of a test to evaluate the efficacy of the anti-TIGIT antibody according to one embodiment at each in vivo dose when administered alone and in combination with an anti-PD-L1 antibody and showing the results indicating efficacy in a CT26 tumor model.

ΔT=Mean tumor volume of test substance-administered group measured on the final day−mean tumor volume of test substance-administered group measured on the administration start day ΔC=Mean tumor volume of negative control-administered group measured on the final day−mean tumor volume of negative control-administered group measured on the administration start day Tumor volume increased approximately 16-fold on the final day in the negative control-administered group, as compared to the administration start day. On the other hand, the group treated with only F04-10 exhibited a slight anti-tumor effect at doses of 3 and 10 mg/kg, and exhibited a maximal effect at a dose of 25 mg/kg, and thus had a strong inhibitory effect on tumor growth. The administration of 10 mg/kg of the anti-PD-L1 antibody alone exhibited a moderate tumor inhibitory effect. When administering the anti-PD-L1 antibody in combination with F04-10 at doses of 3 and 10 mg/kg, the inhibitory effect on tumor growth was stronger as compared to administration of the same dose of F04-10 alone. On the other hand, 25 mg/kg of F04-10, which exhibited the highest effect, did not show an increase in effects upon the combination with the anti-PD-L1 antibody (FIG. 9).

In conclusion, the antibody F04-10 produced in Example exhibited a significant maximum inhibitory effect at 25 mg/kg when administered alone, while the antibody F04-10 administered at doses of 3 and 10 mg/kg lower than 25 mg/kg, exhibited improved effects upon administration in combination with the anti-PD-L1 antibody compared to administration alone.

The statistical analysis shown in FIG. 9 was carried out by Dunnett's multiple comparison using GraphPad Prism 5, and the statistical significance of the difference with respect to the negative control-administered group was expressed as follows. *: $p<0.05$

INDUSTRIAL AVAILABILITY

The anti-TIGIT antibody or the antigen-binding fragment thereof according to the present invention has been found to bind very specifically and strongly to TIGIT and exhibits excellent therapeutic efficacy, as compared to conventional anti-TIGIT antibodies. Accordingly, the pharmaceutical composition containing the anti-TIGIT antibody or an antigen-binding fragment thereof according to the present invention as an active ingredient can be used as an anti-cancer immunotherapeutic agent based on immune cell activation.

In addition, the pharmaceutical composition containing the anti-TIGIT antibody and an antigen-binding fragment thereof according to the present invention as an active ingredient can be used in combination therapy with chemical medicines and other chemotherapeutic agents.

Although specific configurations of the present invention have been described in detail, those skilled in the art will appreciate that this description is provided as preferred embodiments for illustrative purposes and should not be construed as limiting the scope of the present invention. Therefore, the substantial scope of the present invention is defined by the accompanying claims and equivalents thereto.

The invention claimed is:

1. An anti-TIGIT antibody or an antigen-binding fragment thereof comprising:
   (1) a heavy chain variable region comprising:
   a heavy chain CDR1 comprising an amino acid sequence set forth in SEQ ID NO: 1;
   a heavy chain CDR2 comprising an amino acid sequence set forth in SEQ ID NO: 3; and
   a heavy chain CDR3 comprising an amino acid sequence set forth in SEQ ID NO: 5; and
   a light chain variable region comprising:
   a light chain CDR1 comprising an amino acid sequence set forth in SEQ ID NO: 7;
   a light chain CDR2 comprising an amino acid sequence set forth in SEQ ID NO: 9; and
   a light chain CDR3 comprising an amino acid sequence set forth in SEQ ID NO: 11; or
   (2) a heavy chain variable region comprising:
   a heavy chain CDR1 comprising an amino acid sequence set forth in SEQ ID NO: 2;
   a heavy chain CDR2 comprising an amino acid sequence set forth in SEQ ID NO: 4; and
   a heavy chain CDR3 comprising an amino acid sequence set forth in SEQ ID NO: 6; and
   a light chain variable region comprising:
   a light chain CDR1 comprising an amino acid sequence set forth in SEQ ID NO: 8;
   a light chain CDR2 comprising an amino acid sequence set forth in SEQ ID NO: 10; and
   a light chain CDR3 comprising an amino acid sequence set forth in SEQ ID NO: 12.

2. The anti-TIGIT antibody or the antigen-binding fragment thereof according to claim 1, comprising:
   a heavy chain variable region comprising an amino acid sequence set forth in SEQ ID NO: 13 or 14; and
   a light chain variable region comprising an amino acid sequence set forth in SEQ ID NO: 15 or 16.

3. The anti-TIGIT antibody or the antigen-binding fragment thereof according to claim 1, wherein the anti-TIGIT antibody is a monoclonal antibody.

4. The anti-TIGIT antibody or the antigen-binding fragment thereof according to claim 1, wherein the antigen-binding fragment is selected from the group consisting of scFv, (scFv)$_2$, scFv-Fc, Fab, Fab' and F(ab')$_2$ of the anti-TIGIT antibody.

5. A pharmaceutical composition for treating a cancer or tumor comprising the anti-TIGIT antibody or the antigen-binding fragment thereof according to claim 1 as an active ingredient.

6. The pharmaceutical composition according to claim 5, wherein the cancer or tumor is selected from skin cancer, liver cancer, hepatocellular carcinoma, stomach cancer, breast cancer, lung cancer, ovarian cancer, bronchial cancer, nasopharyngeal cancer, laryngeal cancer, pancreatic cancer, bladder cancer, colorectal cancer, colon cancer, cervical cancer, brain cancer, prostate cancer, bone cancer, thyroid cancer, parathyroid cancer, kidney cancer, esophageal cancer, cholangiocarcinoma, testicular cancer, rectal cancer, head and neck cancer, cervical cancer, ureteral cancer, osteosarcoma, neuroblastoma, fibrosarcoma, rhabdomyosarcoma, astrocytoma, neuroblastoma, and glioma.

7. A composition for co-administration for treating a cancer or tumor comprising the anti-TIGIT antibody or the antigen-binding fragment thereof according to claim 1, and other therapeutic agent for cancer.

8. The composition according to claim 7, wherein the other therapeutic agent for cancer is an immune checkpoint inhibitor.

9. The composition according to claim 8, wherein the immune checkpoint inhibitor is an anti-CTLA-4 antibody, an anti-PD-1 antibody or an anti-PD-L1 antibody.

10. An antibody-drug conjugate comprising the anti-TIGIT antibody or the antigen-binding fragment thereof according to claim 1.

11. A composition for treating a cancer or tumor comprising the antibody-drug conjugate according to claim 10.

12. A nucleic acid encoding the anti-TIGIT antibody or the antigen-binding fragment thereof according to claim 1.

13. A recombinant expression vector comprising the nucleic acid according to claim 12.

14. A host cell transformed with the recombinant expression vector according to claim 13.

15. The host cell according to claim 14, wherein the host cell is selected from the group consisting of animal cells, plant cells, yeast, *Escherichia coli* and insect cells.

16. The host cell according to claim 15, wherein the host cell is selected from the group consisting of monkey kidney cells (COS 7), NSO cells, SP2/0 cells, Chinese hamster ovary (CHO) cells, W138, baby hamster kidney (BHK) cells, MDCK, myeloma cell lines, HuT 78 cells, HEK293 cells, *Escherichia coli, Bacillus subtilis, Streptomyces* sp., *Pseudomonas* sp., *Proteus mirabilis, Staphylococcus* sp., *Aspergillus* sp., *Pichia pastoris, Saccharomyces cerevisiae, Schizosaccharomyces* sp. and *Neurospora crassa.*

17. A method for producing an anti-TIGIT antibody or an antigen-binding fragment thereof comprising culturing the host cell according to claim 14.

* * * * *

UNITED STATES PATENT AND TRADEMARK OFFICE
CERTIFICATE OF CORRECTION

| | |
|---|---|
| PATENT NO. | : 11,505,603 B2 |
| APPLICATION NO. | : 16/970351 |
| DATED | : November 22, 2022 |
| INVENTOR(S) | : Kwang-Hoon Lee et al. |

It is certified that error appears in the above-identified patent and that said Letters Patent is hereby corrected as shown below:

In the Specification

Column 10, Line 33, "(COST)" should be -- (COS7) --.
Column 24, Line 15, "564-39-IgG1" should be -- S64-39-IgG1 --.
Column 24, Line 16, "564-39-IgG4" should be -- S64-39-IgG4 --.
Column 24, Line 24, "564-39-IgG1" should be -- S64-39-IgG1 --.
Column 25, Line 23, "564-39-IgG1" should be -- S64-39-IgG1 --.
Column 25, Lines 25-26, "564-39-IgG4" should be -- S64-39-IgG4 --.
Column 27, Line 5, "$\Delta c$" should be -- $\Delta C$ --.
Column 28, Line 30, "Example" should be -- Example 2 --.

In the Claims

Column 56, Line 39, "(COS 7)" should be -- (COS7) --.

Signed and Sealed this
Fourteenth Day of February, 2023

Katherine Kelly Vidal
*Director of the United States Patent and Trademark Office*